United States Patent
Wu et al.

(10) Patent No.: US 10,953,109 B2
(45) Date of Patent: Mar. 23, 2021

(54) APPLICATION OF GPR45 GENE

(71) Applicant: FUDAN UNIVERSITY, Shanghai (CN)

(72) Inventors: Xiaohui Wu, Shanghai (CN); Tian Xu, Shanghai (CN); Min Han, Shanghai (CN); Jing Cui, Shanghai (CN); Tongruei Li, Shanghai (CN)

( * ) Notice: Subject to any disclaimer, the term of this patent is extended or adjusted under 35 U.S.C. 154(b) by 0 days.

(21) Appl. No.: 16/402,217

(22) Filed: May 2, 2019

(65) Prior Publication Data

US 2019/0343969 A1 Nov. 14, 2019

Related U.S. Application Data

(63) Continuation of application No. 15/271,583, filed on Sep. 21, 2016, now abandoned.

(30) Foreign Application Priority Data

Sep. 22, 2015 (CN) .......................... 20151060719.6

(51) Int. Cl.
| | | |
|---|---|---|
| *A01K 67/00* | (2006.01) | |
| *A01K 67/027* | (2006.01) | |
| *A61K 49/00* | (2006.01) | |
| *C12N 15/00* | (2006.01) | |

(52) U.S. Cl.
CPC ...... *A61K 49/0008* (2013.01); *A01K 67/0276* (2013.01); *A01K 2217/052* (2013.01); *A01K 2217/056* (2013.01); *A01K 2217/075* (2013.01); *A01K 2217/206* (2013.01); *A01K 2227/10* (2013.01); *A01K 2227/105* (2013.01); *A01K 2267/0362* (2013.01); *C12N 2800/90* (2013.01)

(58) Field of Classification Search
CPC ............ A61K 49/0008; A01K 67/0276; A01K 2227/105; A01K 2217/075; A01K 2267/0362; C12N 2800/90
See application file for complete search history.

(56) References Cited

U.S. PATENT DOCUMENTS

2006/0134109 A1* 6/2006 Gaitanaris et al.
2010/0154070 A1* 6/2010 Xu et al.

OTHER PUBLICATIONS

Cui J et al. Disruption of Gpr45 causes reduced hypothalamic POMC expression and obesity. J. Clin. Invest. 126:3192-3206, (Year: 2016).*
Sun L et al. PBmice: an integrated database system of piggyBac (PB) insertional mutations and their characterizations in mice. Nucleic Acids Research 36:D729-D734, (Year: 2007).*
Ding S et al. Efficient transposition of the piggyBac (PB) transposon in mammalian cells and mice. Cell 122:473-483, (Year: 2005).*
Lutz T et al. Overview of animal models of obesity. Curr. Protoc. Pharmacol. doi:10.1002/0471141755.ph0561s58; 22 pages, (Year: 2012).*

* cited by examiner

*Primary Examiner* — Quang Nguyen
(74) *Attorney, Agent, or Firm* — Global IP Services; Tianhua Gu

(57) ABSTRACT

The present invention relates to the field of biotechnology, in particular to application of a GPR45 gene. The present invention discloses, for the first time, a correlation between GPR45 and obesity and also discloses that obesity may be caused if the GPR45 gene is knocked out or the expression of the GPR45 gene is reduced. Moreover, an obese mouse model is established by adopting a method of blocking the expression of the GPR45 gene for the first time, which is more similar to the mechanism underlying the obesity of human, is thus an ideal model for obesity basis and clinical application researches and can be well applied in screening of drugs for treating obesity.

5 Claims, 14 Drawing Sheets

Specification includes a Sequence Listing.

SEQUENCE LISTING

```
<160> NUMBER OF SEQ ID NOS: 37

<210> SEQ ID NO 1
<211> LENGTH: 30
<212> TYPE: DNA
<213> ORGANISM: Artificial
<220> FEATURE:
<223> OTHER INFORMATION: LF1

<400> SEQUENCE: 1
cttgaccttg ccacagagga ctattagagg                                    30

<210> SEQ ID NO 2
<211> LENGTH: 30
```

-continued

```
<212> TYPE: DNA
<213> ORGANISM: Artificial
<220> FEATURE:
<223> OTHER INFORMATION: LR1

<400> SEQUENCE: 2
cagtgacact taccgcattg acaagcacgc                                      30

<210> SEQ ID NO 3
<211> LENGTH: 30
<212> TYPE: DNA
<213> ORGANISM: Artificial
<220> FEATURE:
<223> OTHER INFORMATION: RF1

<400> SEQUENCE: 3
cctcgatata cagaccgata aaacacatgc                                      30

<210> SEQ ID NO 4
<211> LENGTH: 30
<212> TYPE: DNA
<213> ORGANISM: Artificial
<220> FEATURE:
<223> OTHER INFORMATION: RR1

<400> SEQUENCE: 4
agtcagtcag aaacaacttt ggcacatatc                                      30

<210> SEQ ID NO 5
<211> LENGTH: 22
<212> TYPE: DNA
<213> ORGANISM: Artificial
<220> FEATURE:
<223> OTHER INFORMATION: GPRE2-1

<400> SEQUENCE: 5
caaacagaaa atgaaagcca cc                                              22

<210> SEQ ID NO 6
<211> LENGTH: 21
<212> TYPE: DNA
<213> ORGANISM: Artificial
<220> FEATURE:
<223> OTHER INFORMATION: GPRE2-2

<400> SEQUENCE: 6
aggaatccta ccacgatcat c                                               21

<210> SEQ ID NO 7
<211> LENGTH: 22
<212> TYPE: DNA
<213> ORGANISM: Artificial
<220> FEATURE:
<223> OTHER INFORMATION: GAPDH-L1

<400> SEQUENCE: 7
tgttcctacc cccaatgtgt cc                                              22

<210> SEQ ID NO 8
<211> LENGTH: 22
<212> TYPE: DNA
<213> ORGANISM: Artificial
<220> FEATURE:
<223> OTHER INFORMATION: GAPDH-1

<400> SEQUENCE: 8
```

```
ggagttgctg aagaagtcgc ag                                             22

<210> SEQ ID NO 9
<211> LENGTH: 19
<212> TYPE: DNA
<213> ORGANISM: Artificial
<220> FEATURE:
<223> OTHER INFORMATION: GPRP1

<400> SEQUENCE: 9
atggcctgta acagcacac                                                 19

<210> SEQ ID NO 10
<211> LENGTH: 19
<212> TYPE: DNA
<213> ORGANISM: Artificial
<220> FEATURE:
<223> OTHER INFORMATION: GPRP2

<400> SEQUENCE: 10
acagtgatga gggtgatgg                                                 19

<210> SEQ ID NO 11
<211> LENGTH: 18
<212> TYPE: DNA
<213> ORGANISM: Artificial
<220> FEATURE:
<223> OTHER INFORMATION: AgRP-F

<400> SEQUENCE: 11
gcggaggtgc tagatcca                                                  18

<210> SEQ ID NO 12
<211> LENGTH: 18
<212> TYPE: DNA
<213> ORGANISM: Artificial
<220> FEATURE:
<223> OTHER INFORMATION: AgRP-B

<400> SEQUENCE: 12
aggactcgtg cagcctta                                                  18

<210> SEQ ID NO 13
<211> LENGTH: 19
<212> TYPE: DNA
<213> ORGANISM: Artificial
<220> FEATURE:
<223> OTHER INFORMATION: NPY-F

<400> SEQUENCE: 13
ctccgctctg cgacactac                                                 19

<210> SEQ ID NO 14
<211> LENGTH: 18
<212> TYPE: DNA
<213> ORGANISM: Artificial
<220> FEATURE:
<223> OTHER INFORMATION: NPY-B

<400> SEQUENCE: 14
aatcagtgtc tcagggct                                                  18

<210> SEQ ID NO 15
<211> LENGTH: 22
<212> TYPE: DNA
<213> ORGANISM: Artificial
```

```
<220> FEATURE:
<223> OTHER INFORMATION: POMC-F2

<400> SEQUENCE: 15
ctgcttcaga cctccataga tg                                        22

<210> SEQ ID NO 16
<211> LENGTH: 19
<212> TYPE: DNA
<213> ORGANISM: Artificial
<220> FEATURE:
<223> OTHER INFORMATION: POMC-B2

<400> SEQUENCE: 16
atctccgttg ccaggaaac                                            19

<210> SEQ ID NO 17
<211> LENGTH: 19
<212> TYPE: DNA
<213> ORGANISM: Artificial
<220> FEATURE:
<223> OTHER INFORMATION: CRAT-F1

<400> SEQUENCE: 17
aaacgcattc cgatctacg                                            19

<210> SEQ ID NO 18
<211> LENGTH: 22
<212> TYPE: DNA
<213> ORGANISM: Artificial
<220> FEATURE:
<223> OTHER INFORMATION: CRAT-B1

<400> SEQUENCE: 18
ggaaagaggg aatatgggaa cc                                        22

<210> SEQ ID NO 19
<211> LENGTH: 20
<212> TYPE: DNA
<213> ORGANISM: Artificial
<220> FEATURE:
<223> OTHER INFORMATION: CRH-F2

<400> SEQUENCE: 19
ctctctggat ctcaccttcc                                           20

<210> SEQ ID NO 20
<211> LENGTH: 22
<212> TYPE: DNA
<213> ORGANISM: Artificial
<220> FEATURE:
<223> OTHER INFORMATION: CRH-B2

<400> SEQUENCE: 20
cttgtgtgct aaatgcagaa tc                                        22

<210> SEQ ID NO 21
<211> LENGTH: 22
<212> TYPE: DNA
<213> ORGANISM: Artificial
<220> FEATURE:
<223> OTHER INFORMATION: TRH-F1

<400> SEQUENCE: 21
tcttgaggaa agacctccag cg                                        22
```

<210> SEQ ID NO 22
<211> LENGTH: 22
<212> TYPE: DNA
<213> ORGANISM: Artificial
<220> FEATURE:
<223> OTHER INFORMATION: TRH-B1

<400> SEQUENCE: 22
aggctcccac ttctcccaaa tc                                              22

<210> SEQ ID NO 23
<211> LENGTH: 22
<212> TYPE: DNA
<213> ORGANISM: Artificial
<220> FEATURE:
<223> OTHER INFORMATION: BDNF-F1

<400> SEQUENCE: 23
catgaaagaa gtaaacgtcc ac                                              22

<210> SEQ ID NO 24
<211> LENGTH: 19
<212> TYPE: DNA
<213> ORGANISM: Artificial
<220> FEATURE:
<223> OTHER INFORMATION: BDNF-B1

<400> SEQUENCE: 24
tcgatgacgt gctcaaaag                                                  19

<210> SEQ ID NO 25
<211> LENGTH: 19
<212> TYPE: DNA
<213> ORGANISM: Artificial
<220> FEATURE:
<223> OTHER INFORMATION: pMCH-F1

<400> SEQUENCE: 25
ggggaaagcc tttcagaag                                                  19

<210> SEQ ID NO 26
<211> LENGTH: 19
<212> TYPE: DNA
<213> ORGANISM: Artificial
<220> FEATURE:
<223> OTHER INFORMATION: pMCH-B1

<400> SEQUENCE: 26
ctgtgtggac tcagcattc                                                  19

<210> SEQ ID NO 27
<211> LENGTH: 22
<212> TYPE: DNA
<213> ORGANISM: Artificial
<220> FEATURE:
<223> OTHER INFORMATION: Orexin-F2

<400> SEQUENCE: 27
ctttccttct acaaaggttc cc                                              22

<210> SEQ ID NO 28
<211> LENGTH: 21
<212> TYPE: DNA
<213> ORGANISM: Artificial
<220> FEATURE:
<223> OTHER INFORMATION: Orexin-B2

-continued

```
<400> SEQUENCE: 28
gctttcccag agtcaggata c                                              21

<210> SEQ ID NO 29
<211> LENGTH: 23
<212> TYPE: DNA
<213> ORGANISM: Artificial
<220> FEATURE:
<223> OTHER INFORMATION: GPR45-siRNAU
ReA4

<400> SEQUENCE: 29
ccgacaucau gcugucuuua utt                                            23

<210> SEQ ID NO 30
<211> LENGTH: 23
<212> TYPE: DNA
<213> ORGANISM: Artificial
<220> FEATURE:
<223> OTHER INFORMATION: GPR45-siRNA74ReA4

<400> SEQUENCE: 30
auaaagacag caugaugucg gtt                                            23

<210> SEQ ID NO 31
<211> LENGTH: 21
<212> TYPE: DNA
<213> ORGANISM: Artificial
<220> FEATURE:
<223> OTHER INFORMATION: RuPT6TUUsiRNAU
ReA4

<400> SEQUENCE: 31
uucuccgaac gugucacgut t                                              21

<210> SEQ ID NO 32
<211> LENGTH: 21
<212> TYPE: DNA
<213> ORGANISM: Artificial
<220> FEATURE:
<223> OTHER INFORMATION: RuPT6TUUsiRNA74ReA4

<400> SEQUENCE: 32
acgugacacg uucggagaat t                                              21

<210> SEQ ID NO 33
<211> LENGTH: 141
<212> TYPE: PRT
<213> ORGANISM: Artificial
<220> FEATURE:
<223> OTHER INFORMATION: ?9T-kD

<400> SEQUENCE: 33

Met Ala Cys Asn Ser Thr Pro Met Gly Thr Tyr Glu His Leu Leu Leu
1               5                   10                  15

Asn Val Ser Asn Thr Leu Asp Pro Gly Asp Thr Pro Leu Ser Ala Pro
            20                  25                  30

Leu Arg Ile Ser Gly Tyr Thr Glu Phe Pro Ala Glu Arg Asn Thr Val
        35                  40                  45

Arg Lys Asn Ala Val Arg Val His Asn Gln Ser Asp Ser Leu Asp Leu
    50                  55                  60

Arg Gln Leu Thr Gly Ala Gly Leu Arg Arg Leu Arg Arg Gln Gln Gln
65                  70                  75                  80
```

Gln Ala Ser Leu Asp Leu Ser Phe Lys Thr Lys Ser Ala Phe Ser Arg
                85                  90                  95

Arg Phe Tyr Tyr Ser Ala Ser Phe Tyr Thr Pro His Thr Phe Gln Ile
            100                 105                 110

Leu Pro Lys Val Pro Glu Arg Ile Gln Arg Lys Ile Gln Pro Ser Thr
        115                 120                 125

Ile Tyr Val Cys Asn Glu Asn Gln Ser Ala Val Leu Glu
130                 135                 140

<210> SEQ ID NO 34
<211> LENGTH: 22
<212> TYPE: DNA
<213> ORGANISM: Artificial
<220> FEATURE:
<223> OTHER INFORMATION: mPBGPR45-CDprimer1

<400> SEQUENCE: 34
accatggcct gtaacagcac ac                                              22

<210> SEQ ID NO 35
<211> LENGTH: 22
<212> TYPE: DNA
<213> ORGANISM: Artificial
<220> FEATURE:
<223> OTHER INFORMATION: mPBGPR45-CDprimer2

<400> SEQUENCE: 35
ctagacagcg gattggtttt cg                                              22

<210> SEQ ID NO 36
<211> LENGTH: 22
<212> TYPE: DNA
<213> ORGANISM: Artificial
<220> FEATURE:
<223> OTHER INFORMATION: HA-F2

<400> SEQUENCE: 36
ccaactggta atggtagcga cc                                              22

<210> SEQ ID NO 37
<211> LENGTH: 22
<212> TYPE: DNA
<213> ORGANISM: Artificial
<220> FEATURE:
<223> OTHER INFORMATION: GPR-B4

<400> SEQUENCE: 37
cgaagggagc aaagaacact gc                                              22

APPLICATION OF GPR45 GENE

CROSS REFERENCE TO RELATED PATENT APPLICATION

This application is a continuation patent application of U.S. Ser. No. 15/271,583 filed Sep. 21, 2016, which claims the priority of CN 2015106071965 filed Sep. 22, 2015.

A sequence listing is filed herewith for the present application. The sequence listing is the same as the sequence listing filed on Dec. 15, 2016 for U.S. Ser. No. 15/271,583.

FIELD OF THE INVENTION

The present invention relates the field of biotechnology, in particular to application of a GPR45 gene.

BACKGROUND OF THE INVENTION

Obesity may cause lots of diseases, including Type 2 diabetes, hepatic steatosis, hypertension, coronary heart disease and various tumors, which jeopardizes health and living quality. Obesity of children and teenagers may further influence adolescent development and sexual maturity. According to statistics of WHO (World Health Organization), 35% of adults in the world are overweight (BMI≥25), more than 10% of adults are obese (BMI≥30) and at least 2.8 million people die from obesity or overweight each year. With the change of lifestyles, obese and overweight populations in China increase rapidly. By calculating according to WHO standards, in 2013, about 28% of adults were overweight, 4-5% of adults were obese and the total number of obese populations had taken the second place in the world in China. By predicting according to the current trend, the proportion of obese populations in 2030 in China may reach 12.6%.

The essential mechanism of obesity is imbalanced individual energy metabolism. It is estimated that genetic factors contribute up to 65% of obesity, but only a small fraction of obese patients have been identified as sufferers of defined obese mutations. Therefore, the mechanisms by which energy balance is shifted upon encountering different stimuli remain to be explored and more efforts are needed in the search for genes that regulate energy balance and obesity. Since the understanding about biological knowledge on occurrence and development mechanism of obesity is limited, there is still a shortage in commonly effective obesity intervention methods at present. For example, it is usually difficult to perform diet and behavior correction for a long time, and effects for diet or behavior correction are always quite different individually. Drugs such as Xenical, Lorcaserin and Qsymia have un-expected side effects on gastrointestinal and cardiovascular systems, and the effects are yet limited. Therefore, after occurrence of obesity, it will always cause a lifelong influence and brings continuous harm to individuals, families and society.

Disease animal models may be greatly helpful to understand disease occurrence and development mechanisms and investigate disease prevention and intervention methods. Genetic operation and phenotypic analysis technology of mice as mammals is the most mature and plays a leading role in development and researches of various disease animal models. However, for a long time, the selection of obese mouse models is extremely limited. A diet-induced obesity model can better simulate the influence of the environment on obesity. However, obesity caused through induction is closely related to the background of strains of mice and components and sources of fat and carbohydrate in feed, and there is a certain difficulty to guarantee the repeatability of working in different laboratories. Compared with the diet-induced obesity model, genetic animal models with spontaneous gene mutation, transgenosis or mutagenesis have higher phenotypic stability and a greater value in researches on disease mechanisms and intervention methods. Commonly used mouse genetic obesity models comprise leptin or leptin receptor mutant ob and db mice, agouti gene mutant $A^y$ mice, MC4R gene knocked-out mice, etc. The ob and db mice gradually become obese around weaning, which leads to insulin resistance and hepatic steatosis. However, the obesity degree varies in different genetic backgrounds. In addition, the ratio of obesity patients with leptin or leptin receptor mutant is extremely low. The lack of leptin signals also contributes to the impossibility to use these two kinds of mice for related signal channel intervention researches. $A^y$ and MC4R gene knocked-out mice have excessive energy intake, yet obesity occurs later than the ob and db mice and the body weight increase is comparatively small. The proportion of obesity patients with MC4R mutation in Northern Europe reaches up to 6%, but it is rare in people in Asia and Mediterranean. When MC4R mutant mice become obese, body length thereof is obviously increased and obesity-related phenotypes such as insulin resistance change greatly with genetic backgrounds of different strains of mice. Mutation agouti protein with an MC4R antagonist function is expressed in brains of $A^y$ mice. It has a similar obesity-related phenotype with MC4R mutant mice. However, the interfere related researches are difficult to perform because of tumors frequently occur in MC4R mutant mice. Therefore, it is always an urgent need to establish novel obesity animal models for disease mechanism and intervention researches in obesity biology obesity animal model.

SUMMARY OF THE INVENTION

In order to overcome the problem existing in the prior art, the purpose of the present invention is to provide new application of a GPR45 gene and use the GPR45 gene for establishment of an obesity animal model.

In order to achieve the above-mentioned purpose and other related purposes, the present invention adopts the following technical solution:

In a first aspect, the present invention provides application of a GPR45 gene to establishment of an obesity animal model.

Preferably, the animals are mammals. More preferably, the mammals are murine. More preferably, the mammals are mice.

The application of separated GPR45 genes to the establishment of the obesity animal model specifically refers to the establishment of the obesity animal model by knocking out GPR45 genes in bodies of the animals or suppressing expression of the GPR45 genes in the bodies of the animals.

The application of separated GPR45 genes to the establishment of the obesity animal model specifically refers to the establishment of the obesity animal model by knocking out the GPR45 genes in the bodies of the animals or suppressing the expression of the GPR45 genes in the bodies of the animals to suppress expression of POMC genes.

In one preferred embodiment of the present invention, the expression of the GPR45 genes is suppressed through PB (piggyBac) transposon insertion mutagenesis. More specifically, the expression of the GPR45 genes is suppressed through PB [Act-RFP] transposon insertion mutagenesis.

Preferably, the obesity animal model can be further developed to form a hepatic steatosis animal model or a diabetes animal model.

In a second aspect, the present invention provides a method for establishing an obesity animal model, comprising the following step: knocking out GPR45 genes in bodies of animals or suppressing expression of the GPR45 genes in the bodies of the animals to obtain the obesity animal model.

Preferably, the animals are mammals. More preferably, the mammals are murine. More preferably, the mammals are mice.

The GPR45 genes can be knocked out or the expression of the GPR45 genes can be suppressed by adopting the existing gene editing methods. For example, the knockout of the GPR45 genes or the reduction of the expression of the GPR45 genes can be realized through insertion of an exogenous DNG segment such as a transposon or a virus in a GPR45 gene sequence or through gene manipulation mediated by a method, e.g., a chemical mutagenesis method such as ENU, or a physical mutagenesis method such X-ray, or a gene targeting method based on an embryonic stem cell or CRISPR/Cas9 technology.

In the embodiment of the present invention, the expression of the GPR45 genes in the bodies of the animals is suppressed through PB transposon insertion mutagenesis. Specifically, the expression of the GPR45 genes in the bodies of the animals is suppressed through PB [Act-RFP] transposon insertion mutagenesis. More specifically, an animal strain provided with a single copy and inserted with PB [Act-RFP] caused by a PB transposon and a transgenic animal strain with PB transposase Act-PBase are used as parental generations to perform mating, then PB insertion sites are identified by using reverse PCR in offspring animals, and an animal strain with a PB transposon inserted in a GPR45 gene intron is identified and screened out such that the obesity animal model can be obtained. Preferably, the PB transposon is inserted at the position of 34,038 bps upstream of the second exon of the GPR45 gene or is inserted at the position of 54,466 bps upstream of the second exon of the GPR45 gene.

In another embodiment of the present invention, the expression of the GPR45 genes is suppressed by means of RNA interference.

Moreover, the gene knockout or the gene expression suppression of the GPR45 genes can be realized by adopting other methods in the prior art, and the method includes, but not limited to the methods listed in the embodiments.

Further, the obesity animal model can be further developed to form a hepatic steatosis animal model or a diabetes animal model.

In a third aspect, the present invention provides an obesity animal model, which is established by adopting the method mentioned as above.

Preferably, the animals are mammals. More preferably, the mammals are murine. More preferably, the mammals are mice.

Preferably, the obesity animal model can be further developed to form a hepatic steatosis animal model or a diabetes animal model.

In a fourth aspect, the present invention provides application of the obesity animal model in screening of weight-reducing drugs.

In a fifth aspect, the present invention provides a method for screening weight-reducing drug candidates, comprising the following steps: administrating test drug candidates to an obesity animal model which is established by adopting the above-mentioned method, and comparing with an obesity animal model to which the test drug candidates are not administrated, wherein test compounds which improve or cure obesity after being administrated are considered as weight-reducing drug candidates.

The screened drug candidates can form a screening library, and cell experiments, animal experiments and/or clinical tests may be further performed to these substances to further confirm and prove weight-reducing effects of the potential substances.

Since the present invention adopts the suppression of the expression of the GPR45 genes to perform induction, the established model is more similar to the pathogenesis mechanism of human and thus is more accurate and efficient in screening of drugs than the existing models. In a sixth aspect, the present invention provides application of a GPR45 gene as an acting target in screening of drugs or preparations for treating obesity.

Preferably, the application specifically refers to using the GPR45 gene as an acting target (or acting object) of drugs or preparations to screen the drugs or preparations to find substances capable of promoting or improving the gene expression or the expression product activity of the GPR45 gene, or change the transcription or the expression or the expression product activity or the cell activity of GPR45 signal downstream gene accordingly as drugs or preparations for treating obesity.

The drugs or preparations for treating obesity can specifically promote or improve the transcription or translation of the GPR45 gene or can specifically promote or improve the expression or activity of GPR45 protein, or change the transcription or the expression or the expression product activity or the cell activity of GPR45 signal downstream gene accordingly, so as to achieve the purpose of treating obesity.

The drug candidates or preparations for treating obesity screened by using the GPR45 gene as the valuable candidate target for obesity intervention include but not limited to nucleic acid molecules, carbohydrates, lipids, small-molecular chemicals, antibody drugs, polypeptides, proteins or viruses.

A dosage of the drugs or preparations for treating obesity is an enough dosage capable of promoting or improving the transcription or translation of the GPR45 gene or promoting or improving the expression or activity of GPR45 protein, or change the transcription or the expression or the expression product activity or the cell activity of GPR45 signal downstream gene accordingly, such that the gene expression or the expression product activity or the cell activity of the GPR45 gene or GPR45 downstream gene can be improved by at least 50%, 80%, 90%, 95% or 99%.

A method for treating obesity by using the drugs or preparations for treating obesity mainly achieves the purpose of treating obesity by using the GPR45 gene as the acting target to promote or improve the expression level or the expression product activity of the GPR45 gene, or change the transcription or the expression or the expression product activity or the cell activity of GPR45 signal downstream gene accordingly. Specifically, during treatment, efficient substances are administrated to patients.

In a seventh aspect, the present invention provides a method for screening drug candidates or preparations for treating obesity, comprising the following steps:
(1) adding a to-be-tested substance into a system for expressing a GPR45 gene; and
(2) detecting a transcription or expression level or the product activity of the GPR45 gene, or a transcription or expression level or the product activity of GPR45 signal downstream gene, or the cell activity in the system, wherein, compared with an experiment in which the to-be-tested substance is not added, if the to-be-tested substance can promote or improve transcription or expression of the GPR45 gene, or change the transcription or the expression or the expression product activity of GPR45 signal downstream gene, or the cell activity accordingly, that the candidate drug can be used as a candidate drug or preparation for treating obesity is indicated.

Compared with the prior art, the present invention has the following beneficial effects: The present invention discloses a correlation between GPR45 and obesity for the first time, and obesity can be caused if the GPR45 gene is knocked out or the expression of the GPR45 gene is suppressed. Moreover, an obese mouse model is established by adopting a method of disrupting the expression of the GPR45 gene for the first time, is more similar to a pathogenesis of human, is an ideal model for obesity basis and clinical application researches and thus can be well applied in screening of drugs for treating obesity.

In addition, the obesity animal model can be further developed to form a hepatic steatosis animal model or a diabetes animal model.

DECRYPTION OF THE EMBODIMENTS

Figure 1:
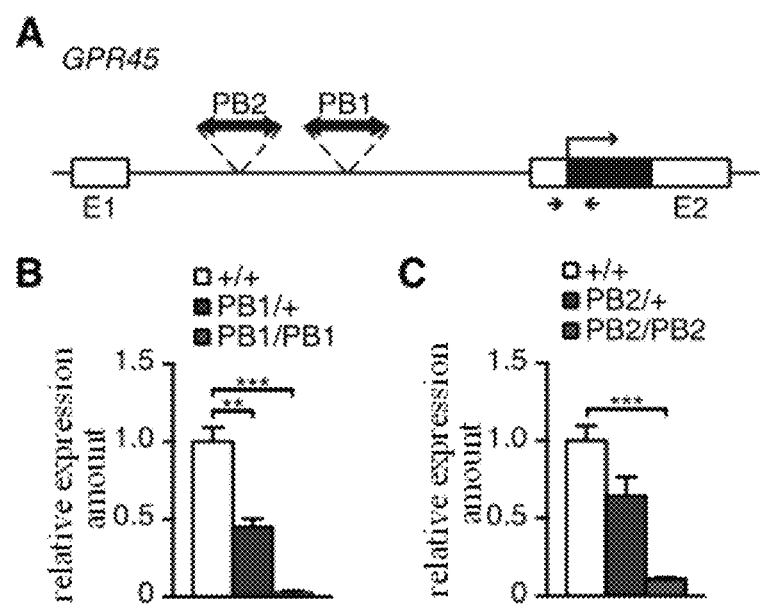
FIG. 1: PB insertion resulted in marked reduction of GPR45 expression, wherein (A) shows a schematic diagram of insertion of a PB transposon in a GPR45 mutant mouse, wherein a coding frame of GPR45 is represented by a black frame, two opposite arrows represent positions of primers for quantitative PCR, a folded line arrow represents a transcription direction and both two PBs (PB1 and PB2) are inserted into an upstream of a second exon (E2); and (B) and (C) respectively show 5-day-old GPR45 mutant full-brain quantitative PCR of a mutant strain 1 (PB1) and a mutant strain 2 (PB2), indicating that expression of homozygote mutant mouse genes is obviously decreased, wherein in each group, from left to right, column lines respectively represent wild type (+/+), heterozygote (PB1/+ or PB2/+) and homozygote (PB1/PB1 or PB2/PB2); a number of mice in each group is greater than or equal to 3, wild-type littermates are selected and used as a control group, GAPDH is internal reference, $p<0.01$; and $*p<0.001$.

Through wide and deep researches, the inventor of the present invention finds that GPR45 (Gene ID: 93690) mutant mice have phenotypes of obesity, hepatic steatosis and diabetes. Disruption of expression of GPR45 results in reduced POMC expression and decreased energy expenditure, and also results in mice obesity. Intraventricular injection of melanotan-2 (MTII), an analog of POMC derived hormones, effectively reverses the obesity caused by GprPR45 mutations. These results revealed an important role of GPR45 in energy homeostasis. The present invention suggests that developing a GPR45-specific agonist may help the treatment of obesity.

The embodiments of the present invention will be described below through specific examples. One skilled in the art can easily understand other advantages and efficacies of the present invention according to contents disclosed in the description. The present invention can also be implemented or applied through other different specific embodiments. Various modifications or variations can be made to all details in the description according to different points of view and applications without departing from the spirit of the present invention. Before further describing the specific embodiments of the present invention, it should be understood that the protection scope of the present invention is not limited to the specific implementation solutions described below; it should also be understood that terms used in the embodiments of the present invention are used for describing the specific implementation solutions instead of limiting the present invention of the present invention; and in the description and claims of the present invention, unless otherwise it is clearly stated, singular forms "one", "a" and "this" include plural forms.

When numerical value ranges are given in the embodiments, it should be understood that, unless otherwise it is stated, two endpoints of each numerical value range and any numerical value between the two endpoints can be selected and used. Unless otherwise it is defined, all technical and scientific terms used in the present invention are the same as meanings which are commonly understood by one skilled in the art. In addition to specific methods, devices and materials used in the embodiments, any methods, devices and materials of the prior art similar to equivalent to the methods, devices and materials in the embodiments of the present invention can also be used to implement the present invention according to the prior art mastered by one skilled in the art and the recorded contents of the present invention.

Unless otherwise it is stated, experiment methods, detection methods, preparation methods disclosed in the present invention adopt conventional molecular biology, biochemistry, chromatin structure and analysis, analytical chemistry, cell culture, recombinant DNA technologies of the art and conventional technologies of the related art. These technologies have been completely described in the existing literatures. Specifically, a reference can be made to: Sambrook, et al., MOLECµAAR CLONING: A LABORATORY MANUAL, Second edition, Cold Spring Harbor Laboratory Press, 1989 and Third edition, 2001; Ausubel, et al., CURRENT PROTOCOLS IN MOLECµAAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECµAAR BIOLOGY, Vol. 119, Chromatin Protocols (P. B. Becker, ed.), Humana Press, Totowa, 1999, etc.

Embodiment 1: Cultivation of GPR45 Inactivated Mutant Mice

GPR45 inactivated mutant mice can be obtained by changing a gene sequence or reducing gene expression through a method of inserting an exogenous DNG segment such as a transposon or a virus in a GPR45 gene sequence, or a chemical mutagenesis method such as ENU, or a physical mutagenesis method such as X-ray, or a gene targeting method based on an embryonic stem cell or CRISPR/Cas9 technology. These methods will cause loss-of-function mutations of GPR45 gene.

In this embodiment, the research strategy is as follows: firstly integrating transposon into a genome, causing precise corresponding gene mutants, then screening out individuals with certain specific phenotypes from the corresponding gene mutants and further detecting an insertion site of the transposon through a reverse PCR technology so as to investigate functions of a mutated gene.

We firstly adopted a mouse strain provided with a single copy and inserted with PB [Act-RFP] caused by a PB transposon and a transgenic mouse strain with PB transposase Act-PBase as parental generations to perform mating to induce PB to transpose in germ cells, then identified a PB insertion site by using reverse PCR in offspring mice and obtained two mutant strains with a PB transposon inserted in a GPR45 gene intron through identification. Specifically, a method for establishing the mouse strain provided with the single copy and inserted with PB [Act-RFP] caused by a PB transposon was as follow:

A method of establishing PB [Act-RFP] comprised the following steps: using a coded sequence of mRFP (A monomeric red fluorescent protein. Campbell R E, Tour O, Palmer A E, Steinbach P A, Baird G S, Zacharias D A, Tsien R Y. Proc Natl Acad Sci USA. 2002 Jun. 11; 99(12):7877-82) to replace an EcoRI segment of 0.7 kb of an eukaryotic vector pCX-EGFP to obtain pCX-RFP; and then cloning a SalI-BamHI segment containing a complete RFP expression original copy from pCX-RFP to a BglII site of pBac-AB to obtain PB[Act-RFP]. For details of the method for establishing the mouse strain provided with the single copy and inserted with PB [Act-RFP] caused by a PB transposon, see Efficient transposition of the piggyBac (PB) transposon in mammalian cells and mice. Ding S, Wu X*, Li G, Han M, Zhuang Y, Xu T*. Cell. 2005 Aug. 12; 122(3):473-83.

A method for establishing the transgenic mouse strain with PB transposase Act-PBase was as follow:
(1) For details of a method for establishing Act-PBase, see Efficient transposition of the piggyBac (PB) transposon in mammalian cells and mice. Ding S, Wu X*, Li G, Han M, Zhuang Y, Xu T*. Cell. 2005 Aug. 12; 122(3):473-83.
(2) For details of the method for establishing the transgenic mouse strain with PB transposase Act-PBase, see Generation of genetically engineered mice by the piggyBac transposon system. Ding S, Xu T, and Wu X. In Mouse Genetics: Methods and Protocols. Singh R S and Coppola V eds. ISBN 978-1-4939-1214-8. Springer. 2014.

For the offspring mice obtained through mating by using the mouse strain provided with the single copy and inserted with PB [Act-RFP] caused by a PB transposon and the transgenic mouse strain with PB transposase Act-PBase as parental generations, mouse tails were shorn to extract genome DNA, and the PB insertion site was identified by using reverse PCR. A specific method comprised the following steps:

shearing and putting a mouse tail in 500 ul of tissue lysate (100 mM NaCl, 100 mMTris, 25 mM EDTA, 0.5% SDS, 125 ug/ml protease K, pH 8.0), and digesting in a 55° C. drying oven overnight;

adding 500 ul of phenol/chloroform/isoamylol (25:24:1), performing fierce oscillation, uniformly mixing and performing centrifugation at temperature of 4° C. and speed of 3000 rpm for 15 min;

taking supernatant, adding chloroform/isoamylol (24:1) with an equal volume, performing fierce oscillation, uniformly mixing and performing centrifugation at speed of 13000 rpm for 15 min;

taking supernatant, adding absolute ethyl alcohol with a double volume for precipitation, turning upside down, and performing centrifugation at room temperature and speed of 13000 rpm for 30 sec;

abandoning supernatant, adding 500 ul of 75% ethyl alcohol and performing centrifugation at room temperature and speed of 13000 rpm for 5 min;

abandoning supernatant and drying at room temperature; adding 100 ul of double distilled water and dissolving at temperature of 55° C. for more than 1 h; and performing enzymatic digestion to genome DNA by using HaeIII of NEB Company at temperature of 37° C. for 6 h, and performing electrophoresis detection, HaeIII thermally inactivated at temperature of 80° C. for 20 min after DNA enzymatic digestion was completed; enzymatic digestion system:

| NEB buffer 2 | 5 ul |
|---|---|
| HaeIII | 2 ul |
| Genome DNA | 2 ug |
| ddH2O | added to 50 ul | enabling enzymatically digested segments to self-connect at 16° C. overnight by using T4 ligase of Takara Company; connecting system:

| T4 ligase buffer | 40 ul |
|---|---|
| T4 ligase | 2 ul |
| Enzymatic digestion product | 40 ul |
| ddH2O | 313 ul | adding 40 ul of 3M NaAc and 1 ml of absolute ethyl alcohol, uniformly mixing, standing at −20° C. for 2 h and performing centrifugation at temperature of 4° C. and speed of 13000 rpm for 15 min;

abandoning supernatant, adding 200 ul of 75% ethyl alcohol and performing centrifugation at room temperature and speed of 13000 rpm for 5 min;

abandoning supernatant and drying at room temperature; adding 150 ul of double distilled water and dissolving at 37° C. for more than 1 h; and performing PCR analysis.

Primers used for obtaining an adjacent genome sequence at a tail end of a left side of a PB transposon were:

```
LF1
                                   (SEQ ID NO. 1)
(5'-CTT GAC CTT GCC ACA GAG GAC TAT TAG AGG-3')

LR1
                                   (SEQ ID NO. 2)
(5'-CAG TGA CAC TTA CCG CAT TGA CAA GCA CGC-3').
```

Primers used for obtaining an adjacent genome sequence at a tail end (PBR) of a right side of a PB transposon were:

```
RF1
                                   (SEQ ID NO. 3)
(5'-CCT CGA TAT ACA GAC CGA TAA AAC ACA TGC-3')

RR1
                                   (SEQ ID NO. 4)
(5'-AGT CAG TCA GAA ACA ACT TTG GCA CAT ATC-3').
```

PCR Reaction System:

| 10 × GT buffer | 2.0 ul |
|---|---|
| DMSO | 2.0 ul |
| 25 mM dNTP | 0.8 ul |
| 20 uM Primers (1/2) | 0.2 ul |
| Taq polymerase | 0.3 ul |
| Template | 1.0 ul |
| ddH2O | 13.5 ul |

Reaction Conditions:

93° C. 90 sec; (93° C. 30 sec, 57° C. 30 sec, 65° C. 3 min)×40 cycles; 65° C. 10 min.

[Note: 10×GT buffer formula: 166 mM $(NH4)_2SO_4$, 670 mMTris (pH 6.8), 67 mM $MgCl_2$, 67 uM EDTA, 50 mM β-mercaptoethanol, sterilized through suction filtration]

PCR products were recovered by using gel extraction, the PCR products were purified by using a gel recovery kit of Tiangen Company, and the PCR products were cloned to pGEM-T vectors (Promega) for sequencing. BLAST comparative analysis was performed to sequencing results by using a mouse genome database in NCBI (National Center of Biotechnology Information) (www.ncbi.nlm.nih.gov) or a genome browser Ensembl of European Bioinformatics Institute (www.ensembl.org).

A GPR45 gene consisted of two exons and a coding frame was located in a second exon of the gene. The two mutant strains obtained by us carried PB [Act-RFP] (Ding S, et al, Cell 122:473, 2005) insert in GPR45 introns, PB of the mutant strain 1 (PB1) was positioned at upstream 34,038 bps of the second exon of the GPR45 gene and PB of the mutant strain 2 (PB2) was positioned at upstream 54,466 bps of the second exon of the GPR45 gene. Since PB was inserted into the only one intron of the GPR45 gene of both two mutant strains, RNA transcription of GPR45 was caused to be blocked.

We detected expression amounts of mRNA of GPR45 genes in whole brains of 5-day-old mice of the two mutant strains. A specific method comprised the following steps:

taking and adding whole brains of 5-day-old mice into 1 ml of Trizol (Ambion Company), uniformly grinding tissue blocks and preserving at −80° C.;

adding 200 ul of $CHCl_3$, oscillating for 15 sec and placing at room temperature for 10 min;

performing centrifugation at speed of 12000 rpm and temperature of 4° C. for 15 min; taking supernatant, adding 500 ul of isopropanol, oscillating for 15 sec and placing at room temperature for 10 min;

performing centrifugation at speed of 12000 rpm and temperature of 4° C. for 15 min; washing with 500 ul of 75% ethyl alcohol, 7500 g, 5 min;

abandoning supernatant and drying total RNA at room temperature;

adding 50 ul of ddH2O (RNase free) and dissolving RNA at temperature of 37° C.; and taking 2 ul for electrophoresis, detecting OD and determining RNA concentration.

A reverse transcription kit (Takara Company, catalogue number: RR047A) was used to extract genome DNA and reverse transcription, and cDNA obtained by reverse transcription was used for an RT-PCR template.

Real-time quantitative PCR system and reaction conditions were adopted by referring to reaction instructions of SYBR Green Master Mix of Agilent Company or Vazyme Company. Data acquisition and result analysis were performed on Mx3000P of Stratagene Company or LightCycler480 II quantitative PCR instrument of Roche Company (at least 3 cases for each genotype, 3 repetitions for each case, standard curves being diluted for four times by adopting double or quadruple gradient). Transcription level of GAPDH gene was selected and used as an internal reference. Specific sequences of used primers were as follows, wherein primers used for amplifying the GPR45 genes in the bodies of the mice of the first mutant strain were called as GPRE2-1, and primers used for amplifying the GPR45 genes in the bodies of the mice of the second mutant strain were called as GPRE2-2:

| GPR45 | GPRE2-1 | CAAACAGAAAATGAAAGCCACC | SEQ ID NO. 5 |
| | GPRE2-2 | AGGAATCCTACCACGATCATC | SEQ ID NO. 6 |
| GAPDH | GAPDH-L1 | TGTTCCTACCCCCAATGTGTCC | SEQ ID NO. 7 |
| | GAPDH-R1 | GGAGTTGCTGAAGAAGTCGCAG | SEQ ID NO. 8 |

As proved by results, the insertion of PB caused the expression levels of mRNA of the GPR45 genes in the bodies of the mice of the two mutant strains to obviously decrease. As shown in FIG. 1, compared with wild type mice, the expression of GPR45 in GPR45$^{PB1/PB1}$ homozygote mutants was decreased by 97.3% and the expression of GPR45 in GPR45$^{PB1/+}$ heterozygote mutants was decreased by 55.2%; and the expression of GPR45 in GPR45$^{PB2}$ homozygote mutants and heterozygote mutants was respectively decreased by 89.4% and 35.7%. To sum up, the insertion of a PB transposon seriously disrupted the expression of the GPR45 genes in the bodies of the mice.

Embodiment 2: Disruption of GPR45$^{PB1}$ Causes Obesity

Figure 2:
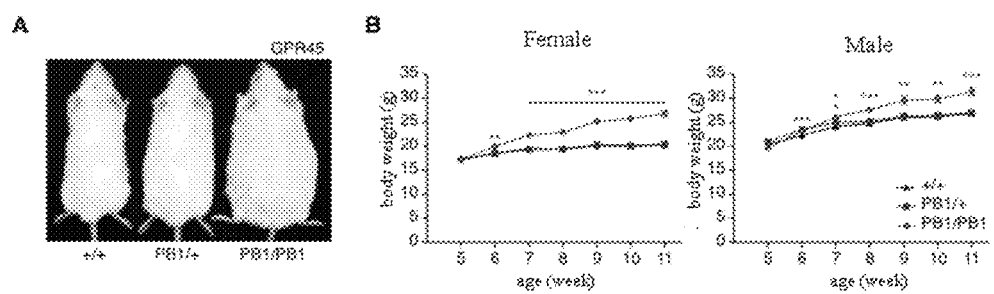
FIG. 2: GPR45$^{PB1}$ mutation results in increased body weight, wherein mice in (A) from left to right respectively represent 1-year-old female homozygote GPR45$^{PB1}$ mouse (PB1/PB1), brood heterozygote mouse (PB1/+) and brood wild type mouse (+/+); and (B) shows body weight increase curves of GPR45$^{PB1}$ mice from age of 5 weeks to age of 11 weeks, wherein body weight of homozygote mice starts to increase obviously from age of 6 weeks, and in each group, from top to bottom, a first curve represents wild type (+/+), a third curve represents heterozygote (PB1/+) and a second curve represents homozygote (PB1/PB1); and a number of mice in each group is greater than or equal to 10, wild-type littermates are selected and used as a control group, $*p<0.05$; $p<0.01$; and $*p<0.001$.

We found that GPR45$^{PB1/PB1}$ homozygote mutants presented serious obesity (as shown in FIG. 2). By weekly detecting body weight of mutant mice and wild-type littermates from age of 5 weeks, it was found that, compared with the wild type mice, the weight of the GPR45$^{PB1/PB1}$ homozygote mutants started to quickly increase from age of about 6 weeks, and when the age of the mice was 11 weeks, the body weight of female homozygote mutants and male homozygote mutants was respectively 33.6% and 16.9% greater than the body weight of the wild type mice. Comparatively, the body weight of the heterozygote mutants and the wild type mice was not obviously different.

Figure 3:
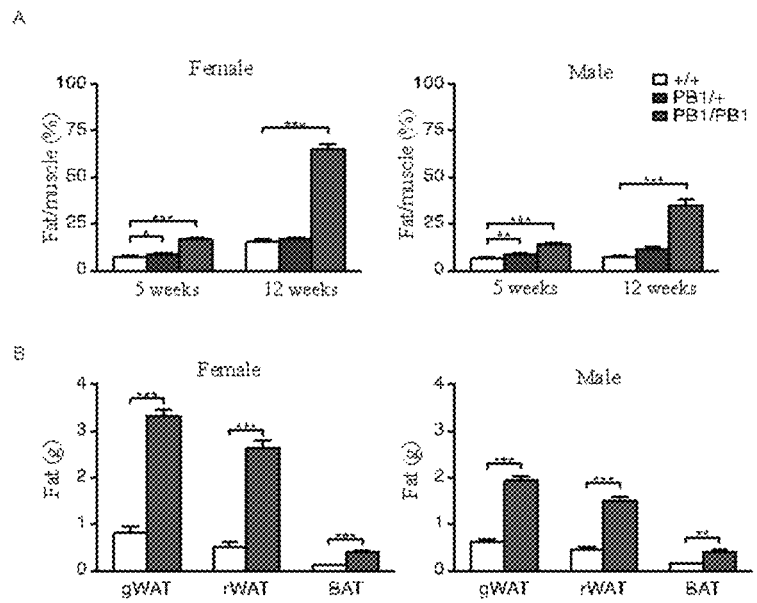
FIG. 3: GPR45$^{PB1}$ mutation results in increased body fat, wherein (A) shows fat-lean ratio of mice from age of 5 weeks to age of 12 weeks, wherein the fat-lean ratio of homozygote mice at age of 5 weeks and age of 12 weeks is obviously increased, in each group, from left to right, a first column line represents wild type+/+, a second column line represents heterozygote (PB1/+), a third column line represents homozygote (PB1/PB1), a number of mice in each group is greater than or equal to 10, wild-type littermates are selected and used as a control group, $*p<0.05$; $p<0.01$; and $*p<0.001$; and (B) shows weight of gonadal white adipose tissues (gWAT), retroperitoneal white adipose tissues (rWAT) and interscapular brown adipose tissues (BAT) of mice at age of 6 months, wherein the weight of gWAT, rWAT and BAT of homozygote mice is obviously increased, in each group, from left to right, a first column line represents wild type (+/+), a second column line represents homozygote (PB1/PB1), a number of mice in each group is greater than or equal to 3, wild-type littermates are selected and used as a control group and $***p<0.001$.

In order to carry out a further research on a tissue component of which the increase causes the increase of the body weight of the mutant mice, we detected body components of 5-week-old and 12-week-old mice by using a nuclear magnetic resonance instrument (as shown in FIG. 3). By calculating fat-lean ratio, it was found that, although the body weight of the 5-week-old mutant mice was not obviously different from the body weight of the wild type mice, the fat-lean ratio had been obviously increased, and the fat-lean ratio of the female mutants and the male mutants was respectively 1.3 times and 1.2 times higher than the fat-lean ratio of the wild type mice. The fat-lean ratio of the 12-week-old mutant mice was higher than the fat-lean ratio of the wild type mice at the same age, and the fat-lean ratio of the female and male mutants was respectively increased by 3.3 times and 3.9 times. The fat-lean ratio of the heterozygote mutant mice was obviously increased to a certain extent. In order to prove the above-mentioned results, we dissected 6-month-old mutant mice and found that the fat tissues of the mutant mice were really and obviously more than the fat tissues of the wild type mice. Gonadal white adipose tissues, retroperitoneal white adipose tissues and interscapular brown adipose tissues of the female homozygote mutant mice were respectively increased by 3.1 times, 4.0 times and 2.2 times relative to the corresponding fat tissues of the wild type mice; and gonadal white adipose tissues, retroperitoneal white adipose tissues and interscapular brown adipose tissues of the male homozygote mutant mice were respectively increased by 2.1 times, 2.3 times and 1.5 times relative to the corresponding fat tissues of the wild type mice. The above-mentioned results fully indicated that the GPR45$^{PB1/PB1}$ homozygote mutants had serious obesity.

To sum up, blocking of expression of GPR45 in mice caused occurrence of obesity.

Embodiment 3: GPR45PB1 Mutation Causes Hepatic Steatosiss

Figure 4:
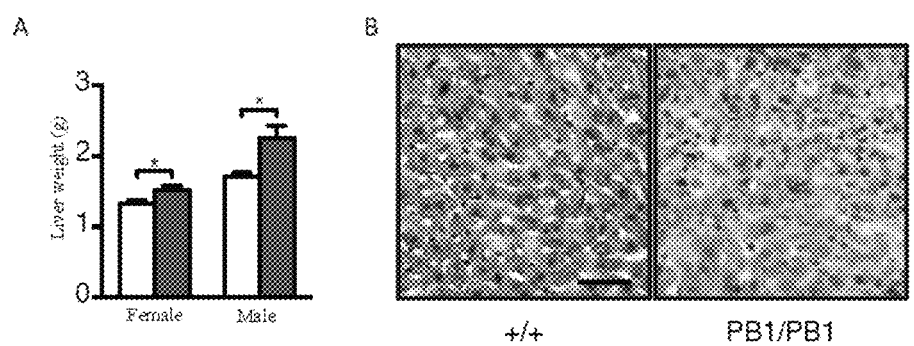
FIG. 4: GPR45$^{PB1}$ mutation results in hepatic steatosiss, wherein (A) shows weight of livers of mice at age of 6 months, wherein it can be seen that the weight of livers of homozygote mice at age of 6 months is obviously increased, in each group, from left to right, a first column line represents wild type (+/+), a second column line represents homozygote (PB1/PB1), a number of mice in each group is greater than or equal to 3, wild-type littermates are selected and used as a control group and $*p<0.05$; and (B) shows oil red staining of liver tissues of mice at age of 6 months, wherein more fat accumulation (red fat drops) occurs in livers of homozygote mice and a scale therein is 0.05 mm.

In obese patients, fat metabolism disorder usually cause excessive accumulation of fat in livers, resulting occurrence of hepatic steatosiss. In order to determine whether occurrence of hepatic steatosiss existed in GPR45$^{PB1}$ mutant mice or not, we dissected livers of the mutant mice and found that the weight of the livers of 6-month-old female homozygote mutant mice and male homozygote mutant mice was respectively increased by 14.4% and 32.2% relative to the weight of the livers of wild type mice. The increase of the weight of the livers indicated that there was a possibility of fat accumulation. In order to further determine that the mutant mice had a phenotype of hepatic steatosiss, we stained frozen slices of livers of 9-month-old mice by using a dye, i.e., oil red O which can stain fat in red (as shown in FIG. 4). Results indicated that more fat drops were accumulated in liver cells of the mutant mice. The above-mentioned results indicated that GPR45$^{PB1}$ mutant mice had serious hepatic steatosiss.

Figure 5:
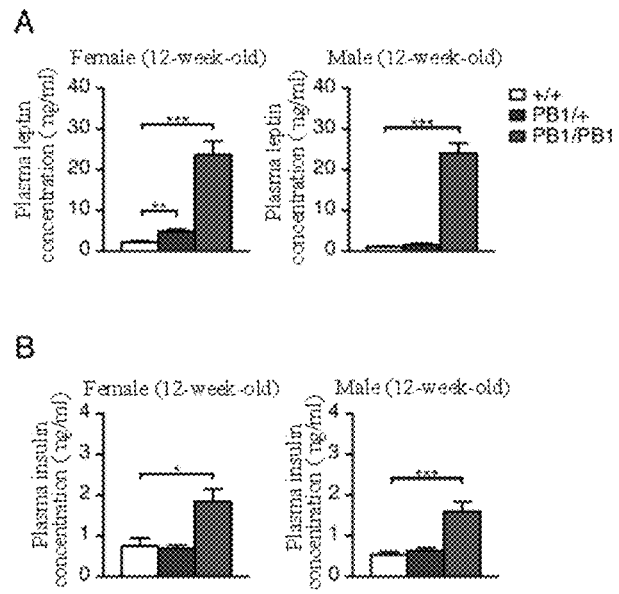
FIG. 5: GPR45$^{PB1}$ mutation results in high leptin and high insulin in plasma, wherein (A) shows content of plasma leptin of 12-week-old mice after fasting and (B) shows content of plasma insulin of 12-week-old mice after fasting, wherein in each group, from left to right, a first column line represents wild type, a second column line represents heterozygote (PB1/+) and a third column line represents homozygote (PB1/PB1); contents of plasma leptin and plasma insulin of 12-week-old homozygote mice obviously rise; a number of mice in each group is greater than or equal to 6, wild-type littermates are selected and used as a control group and $p<0.01$; and $*p<0.001$.

Embodiment 4: GPR45$^{PB1}$ Mutation Causes High Leptin and High Insulin Level in Plasma Leptin and insulin are two important hormones for balancing fat metabolism and glucose metabolism. Leptin in serum of most obese patients increases, and a symptom of increase of insulin in obese and Type 2 diabetes patients is often detected. In order to detect the levels of leptin and insulin in bodies of GPR45$^{PB1}$ mutant mice, we detected the concentrations of the two hormones in serum of 12-wee-old mutant mice by using ELISA (Enzyme-Linked Immune-Sorbent Assay) (as shown in FIG. 5). The levels of leptin in serum of female mutant mice and male mutant mice after being hungered were respectively 9.9 times and 23.8 times higher than level of leptin in serum of wild type mice; and the levels of insulin in serum were respectively 1.5 times and 2 times higher. As proved by experiments, blocking of expression of GPR45 in bodies of mice caused phenotypes of high leptin and high insulin.

Figure 6:
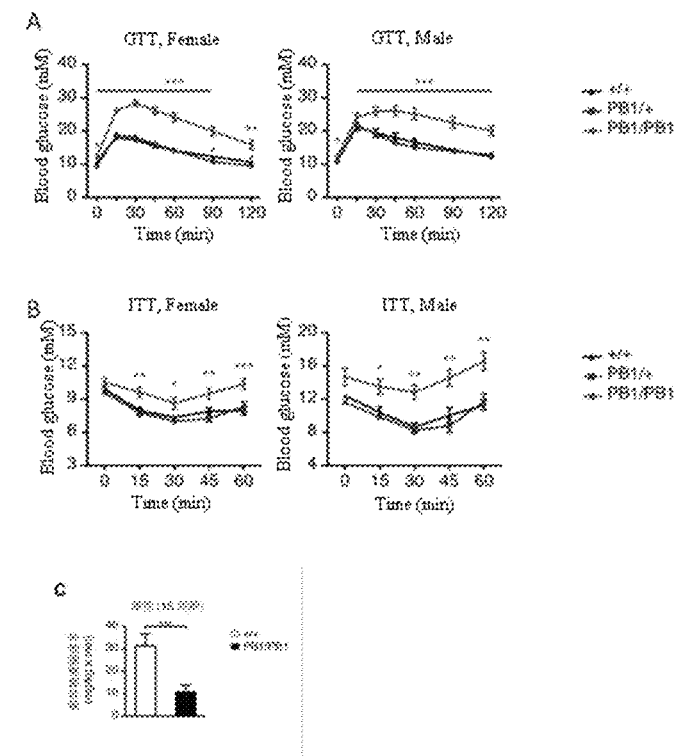
FIG. 6: GPR45$^{PB1}$ mutation results in impaired glucose homeostasis and insulin resistance, wherein (A) shows results of glucose tolerance tests of 12-week-old fasted GPR45$^{PB1}$ mice, wherein homozygote mice present serious glucose intolerance; (B) shows results of insulin tolerance tests of 15-week-old freely fed GPR45$^{PB1}$ mice, wherein homozygote mice present insulin insensitivity; (C) shows results of hyperinsulinemic-euglycemic clamp tests of 15-week-old freely fed GPR45$^{PB1}$ mice, wherein homozygote mice present the decrease of glucose perfusion rate (insulin resistance); a number of mice in each group is greater than or equal to 5, wild-type littermates are selected and used as a control group and $*p<0.05$; $p<0.01$; and $*p<0.001$.

Embodiment 5: GPR45$^{PB1}$ Mutation Causes Insulin Resistance and Glucose Intolerance Insulin resistance is an important cause of glucose metabolism imbalance of Type 2 diabetes patients. Insulin resistance usually causes increase of insulin in serum and is reflected as high insulin. In order to detect whether insulin response of GPR45$^{PB1}$ mutant mice was influenced or not, we detected sensitivity degrees of insulin response of 15-week-old mutant mice by using an ITT (Insulin Tolerance Test) (as shown in FIG. 6). We injected insulin into abdominal cavities of mutant mice and wild type mice and then monitored change of blood glucose of the mice. We found that not only was the level of blood glucose of the mutant mice always above the level of blood glucose of the wild type mice, but also the decrease speed of the blood glucose of the mutant mice was obviously lower than the decrease speed of the blood glucose of the wild type mice after the injection of insulin. We further perform hyperinsulinemic-euglycemic clamp tests to detect the insulin sensitivity of 15-week-old male mice (as shown in FIG. 6), the glucose perfusion rate of homozygote mice decreases by 66% comparing with the wild type mice. As provided by the above-mentioned experiments, GPR45$^{PB1}$ mutant mice had a phenotype of insulin resistance.

We found that, during the insulin tolerance test, the blood glucose of freely fed mutant mice was obviously higher than the blood glucose of the wild type mice. The increase of blood glucose indicated that a glucose metabolism balance capacity was damaged. In order to prove this conclusion, we detected the glucose tolerance capacity of 12-week-old GPR45$^{PB1}$ mutant mice by using a GTT (Glucose Tolerance Test) (as shown in FIG. 6). After the mice were hungered for 16 h, fasting blood glucose of the mice was detected, and the blood glucose of female mutant mice and male mutant mice was respectively 16.5% and 13.7% higher than the blood glucose of the wild type mice. Thereafter, glucose was injected into abdominal cavities of the mice, the change of blood glucose of the mice was monitored and we found that, after the glucose was injected, the blood glucose of the mutant mice rapidly increased and the increase speed of the blood glucose was obviously higher than the increase speed of the blood glucose of the wild type mice. After 30 min after the glucose was injected, the level of blood glucose reached a peak value, then the blood glucose was eliminated by the insulin in serum and the level of blood glucose gradually decreased, but the elimination speed of the blood glucose of the mutant mice was obviously lower than the elimination speed of the blood glucose of the wild type mice. The above-mentioned results indicated that the glucose metabolism capacity of GPR45$^{PB1}$ mutant mice was weakened.

Figure 7:
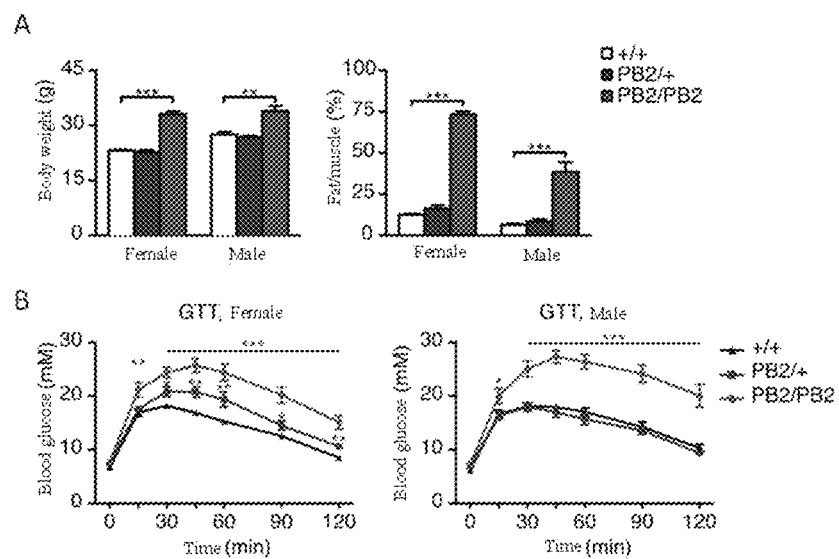
FIG. 7: GPR45$^{PB2}$ mutation also results in obesity and impaired glucose homeostasis, wherein (A) shows body weight and fat-lean ratio of 12-week-old GPR45$^{PB2}$ mice, wherein homozygote mice present overweight and obesity, in each group of (A), from left to right, a first column line represents wild type (+/+), a second column line represents heterozygote (PB2/+) and a third column line represents homozygote (PB2/PB2); (B) shows results of glucose tolerance tests of 12-week-old fasted GPR45$^{PB2}$ mice, wherein homozygote mice present serious glucose intolerance, a number of mice in each group is greater than or equal to 6, wild-type littermates are selected and used as a control group and $*p<0.05$; $p<0.01$; and $*p<0.001$.

Embodiment 6: GPR45$^{PB2}$ Mutation Also Causes Obesity and Glucose Intolerance Besides, we also detected the body weight and fat-lean ratio of 12-week-old GPR45$^{PB2/PB2}$ mutant mice (as shown in FIG. 7). Results indicated that the mutant mice and GPR45$^{PB1/PB1}$ mutant mice had the similar phenotype of obesity. Compared with wild type mice, the body weight of 12-week female homozygote mutants and male homozygote mutants was respectively 43.0% and 23.4% greater than the body weight of the wild type mice, and the fat-lean ratio of the 12-week female homozygote mutants and male homozygote mutants was respectively 4.8 times and 5 times higher than the fat-lean ratio of the wild type mice. We simultaneously detected the glucose tolerance capacity of the 12-week-old GPR45$^{PB2/PB2}$ mutant mice and also obtained the similar results (as shown in FIG. 7).

Embodiment 7: Genetic Revertant of GPR45 or Transgenic Expression Results in Reduced Obesity of Mice To sum up from embodiments 1-6, we observed that GPR45$^{PB1}$ and GPR45$^{PB2}$ mutant mice had the similar phenotypes of obesity and glucose intolerance. Therefore, we deduced that blocking of expression of GPR45 was closely related to the phenotype of obesity of the mutant mice. In order to further prove this assumption, we enabled transgenic mice carrying PBase transposase to mate with GPR45$^{PB1}$ homozygote mutant mice, obtained GPR45$^{PB1}$ homozygote mutant mice carrying PBase genes, then enabled the GPR45$^{PB1}$ homozygote mutant mice carrying PBase genes to mate with GPR45$^{PB1}$ homozygote mutant mice and obtained a GPR45 reverse mutant strain (GPR$^{rev/}$ GPR$^{rev}$) which was produced by precise removal of the inserted PB transposon.

A method for establishing transgenic mice carrying PB transposase was as follow:
(1) For details of a method for establishing Act-PBase, see Efficient transposition of the piggyBac (PB) transposon in mammalian cells and mice. Ding S, Wu X*, Li G, Han M, Zhuang Y, Xu T*. Cell. 2005 Aug. 12; 122(3):473-83.
(2) For details of a method for establishing transgenic mice carrying PBase transposase, see Generation of genetically engineered mice by the piggyBac transposon system. Ding S, Xu T, and Wu X. In Mouse Genetics: Methods and Protocols. Singh R S and Coppola V eds. ISBN 978-1-4939-1214-8. Springer. 2014.

Figure 8:
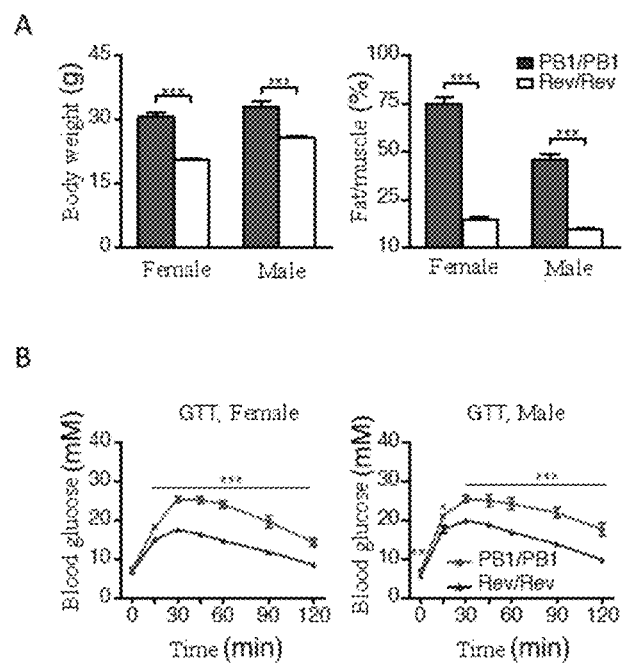
FIG. 8: accurate excision of PB1 suppresses occurrence of obesity and impaired glucose homeostasis, wherein (A) body weight and fat-lean ratio of 12-week-old reverse mutant mice (Rev/Rev), wherein obesity degrees of reverse mutant mice are relieved, in each group, from left to right, a first column line represents homozygote (PB1/PB1) and a second column line represents reverse mutant strain (Rev/Rev); (B) shows results of glucose tolerance tests of 12-week-old fasted reverse mutant mice, wherein reverse mutant mice present improved glucose tolerance, a number of mice in each group is greater than or equal to 6, brood PB1-unexcised homozygote mice are selected and used as a control group and $*p<0.05$; $p<0.01$; and $*p<0.001$.

We detected the body weight and fat-lean ratio of 12-week-old reverse mutant mice and found that the body weight and fat-lean ratio of homozygote reverse mutant mice obviously decreased relative to GPR45$^{PB1/PB1}$ homozygote mutant mice and were not obviously different from the body weight and fat-lean ratio of the wild type mice; and we simultaneously detected the glucose tolerance capacity of the 12-week-old reverse mutant mice and found that, compared with the GPR45$^{PB1/PB1}$ homozygote mutant mice, the glucose tolerance capacity of the reverse mutant mice was obviously enhanced and was basically similar to the glucose tolerance capacity of the wild type mice. As proved by the above-mentioned experiments, blocking of expression of GPR45 caused metabolism disorder (as shown in FIG. 8).

In order to further prove the above-mentioned experiment results, we established GPR45 transgenic mice (NSE:: GPR45) by using an NSE (Neuron Specific Enolase) promoter: adult mouse whole-brain cDNA was used as a PCR template, two pairs of primers which are mGPR45CDprimer1 and mGPR45CDprimer2 were used to amplify mouse GPR45 full-length coding sequences (for the PCR method, refer to operation instructions of KOD-Plus-Ver.2 high-fidelity polymerase of TOYOBO Company), the sequences were connected into T vectors for sequencing, and positive plasmids were enzymatically digested by using EagI and then were flatly connected into pcDNA4.0-HA vectors to obtain pcDNA4.0-HA-GPR45. Then, pcDNA4.0-HA-GPR45 was enzymatically digested by using NheI/EcoRV to obtain HA-GPR45 segments, and then the HA-GPR45 segments were flatly connected into HindIII sites of pNSE vectors (SUN1 and SUN2 play critical but partially redundant roles in anchoring nuclei in skeletal muscle cells in mice. Lei K, Zhang X, Ding X, Guo X, Chen M, Zhu B, Xu T, Zhuang Y, Xu R, Han M. Proc Natl Acad Sci USA. 2009 Jun. 23; 106(25):10207-12). Plasmids were linearized by using NotI and then were injected into FVB/NJ mouse fertilized eggs, the injection method was consistent with the method for establishing the transgenic mice carrying Act-PBase, founder mice were obtained and identification was performed by using two pairs of primers which are HA-F2 and GPR-B4 (the PCR method was the same as GT-PCR reaction described above).

| | | |
|---|---|---|
| mPBGPR45-CDprimer1 | ACCATGGCCTGTAACAGCACAC | SEQ ID NO. 34 |
| mPBGPR45-CDprimer2 | CTAGACAGCGGATTGGTTTTCG | SEQ ID NO. 35 |
| HA-F2 | CCAACTGGTAATGGTAGCGACC | SEQ ID NO. 36 |
| GPR-B4 | CGAAGGGAGCAAAGAACACTGC | SEQ ID NO. 37 |

Figure 28:
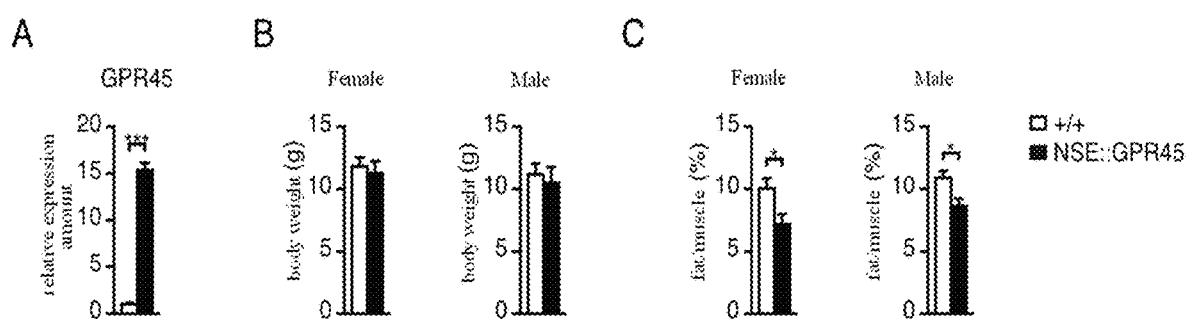
FIG. 28: obesity is suppressed through expression of GPR45 in neurons, wherein (A) shows expression amounts of GPR45 in hypothalamus of 5-day-old NSE::GPR45 transgenic mice, wherein RT-PCR results indicate that expression amounts of GPR45 in hypothalamus of transgenic mice increase; (B) shows that body weight of 21-day-old NSE::GPR45 transgenic mice is normal; (C) shows that fat-lean ratio of 21-day-old NSE::GPR45 transgenic mice obviously decreases; in each group, from left to right, a first column line represents wild type (+/+), a second column line represents transgene (NSE::GPR45), a number of mice in each group is greater than or equal to 3, wild-type littermates are selected and used as a control group and *$p<0.05$; $p<0.01$; and *$p<0.001$.

Compared with the wild type mice, the expression amounts of GPR45 in hypothalamus of 5-day-old transgenic mice increased by 15.4 times (as shown in FIG. 28). Simultaneously, we detected the body weight and fat-lean ratio of 3-week-old transgenic mice (as shown in FIG. 28). Results indicated that, although the body weight of the 3-week-old NSE::GPR45 transgenic mice was similar to the body weight of the wild-type littermates, the body fat content obviously decreased; and the fat-lean ratio of female and male mice respectively decreased by 28.6% and 20.6%. The results indicated that expression of GPR45 in neurons can suppress accumulation of fat in mice.

To sum up, PB insertion mutation disrupted expression of GPR45 and caused the mice to present phenotypes of metabolism disorders such as obesity, hepatic steatosiss, glucose intolerance and insulin resistance, indicating that GPR45 participated in regulation of body energy metabolism balance. Whereas the phenotypes of GPR45$^{PB2/PB2}$ mice were similar to the phenotypes of GPR45$^{PB1/PB1}$ mice, the GPR45$^{PB1/PB1}$ mice were selected as the mice which were used for researches below.

Embodiment 8: Obesity is a Primary Phenotype of GPR45 Mutant Mice

As everyone knows, fat metabolism disorder usually causes impaired glucose homeostasis and impaired glucose homeostasis also influences fat metabolism. For example, obesity increases risks of insulin resistance and Type 2 diabetes, and mouse skeletal muscle specific insulin resistance also causes excessive accumulation of fat. In addition, hepatic steatosiss and insulin resistance are closely related to occurrence of obesity related diseases. Exploration of the primary phenotype of GPR45 mutant mice helps us to find the root cause of GPR45 metabolism disorder.

Figure 9:
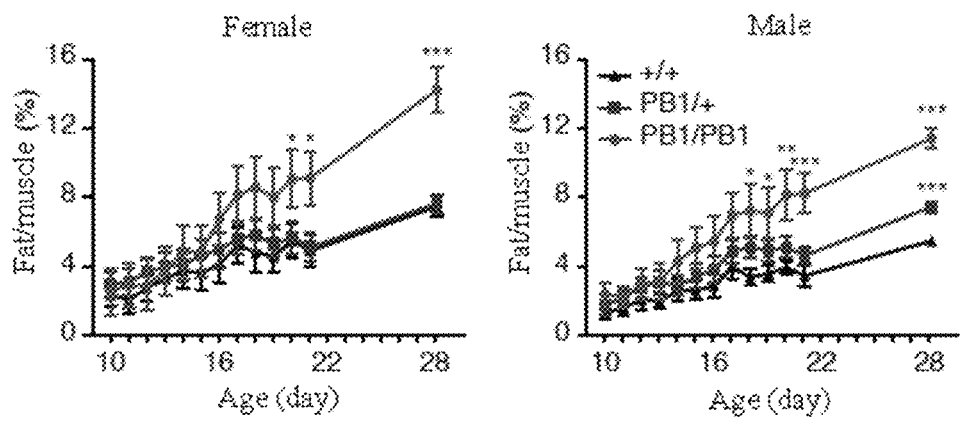
FIG. 9: obesity of GPR45$^{PB1/PB1}$ mice occurs before weaning, shows growth curves of fat-lean ratio of mice from age of 10 days to age of 28 days, wherein homozygote female mice present obesity from age of 20 days, male mice present obesity from age of 18 days, a number of mice in each group is greater than or equal to 6, wild-type littermates are selected and used as a control group and $*p<0.05$; $p<0.01$; and $*p<0.001$.

Firstly, we monitored time of occurrence of obesity in mice. As proved by the above-mentioned experiment results, although the body weight of 5-week-old GPR45$^{PB1/PB1}$ mice was not different from the body weight of wild type mice, the fat-lean ratio had already been obviously higher than the fat-lean ratio of the wild type mice. In order to find the age from which the mice started to become obese, we monitored the fat-lean ratio of mutant mice from age of 10 days to age of 28 days (as shown in FIG. 9). Results indicated that, although the fat-lean ratio of the mutant mice at the beginning was not obviously different from the fat-lean ratio of the wild type mice, the increase of the fat-lean ratio of the mutant mice was obviously quicker than that of the wild type mice. The fat-lean ratio of 20-day-old female and 18-day-old male mice was obviously higher than that of the wild type mice, indicating that the female mutant mice and the male mutant mice respectively become obese from the 20th day and the 18th day.

Figure 10:
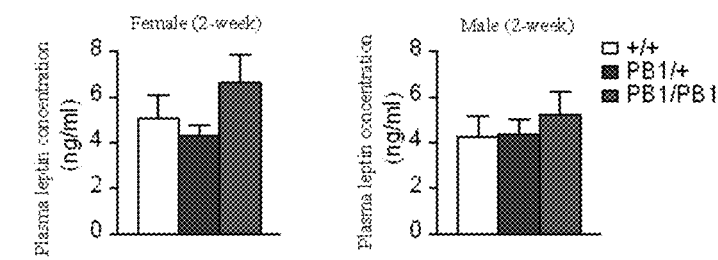
FIG. 10: plasma leptin level elevated after obesity of GPR45$^{PB1/PB1}$ mice occurs, wherein (A) shows that plasma leptin level of 2-week-old GPR45$^{PB1/PB1}$ mice is normal; (B) shows that plasma leptin level of 4-week-old GPR45$^{PB1/PB1}$ mice rises, from left to right, a first column line represents wild type (+/+), a second column line represents heterozygote (PB1/+) and a third column line represents homozygote (PB1/PB1); a number of mice in each group is greater than or equal to 6, wild-type littermates are selected and used as a control group and $*p<0.05$; and $***p<0.001$.
Figure 10:
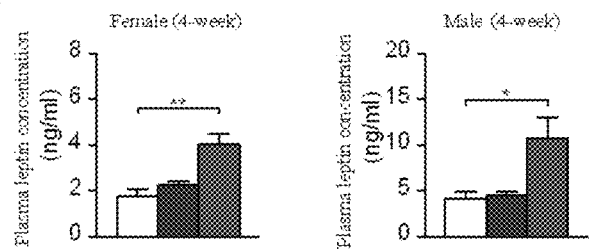

Simultaneously, we detected the level of leptin in serum of mice after being hungered and found that the level of leptin in serum of 14-day-old mutant mice was not greatly different from that of the wild type mice, but after two weeks, the level of leptin in serum of female and male mutant mice was respectively increased by 1.3 time and 1.6 times relative to that of the wild type mice (as shown in FIG. 10). The above-mentioned results indicated that GPR45 mutant mice presented the phenotype of obesity before weaning.

Figure 11:
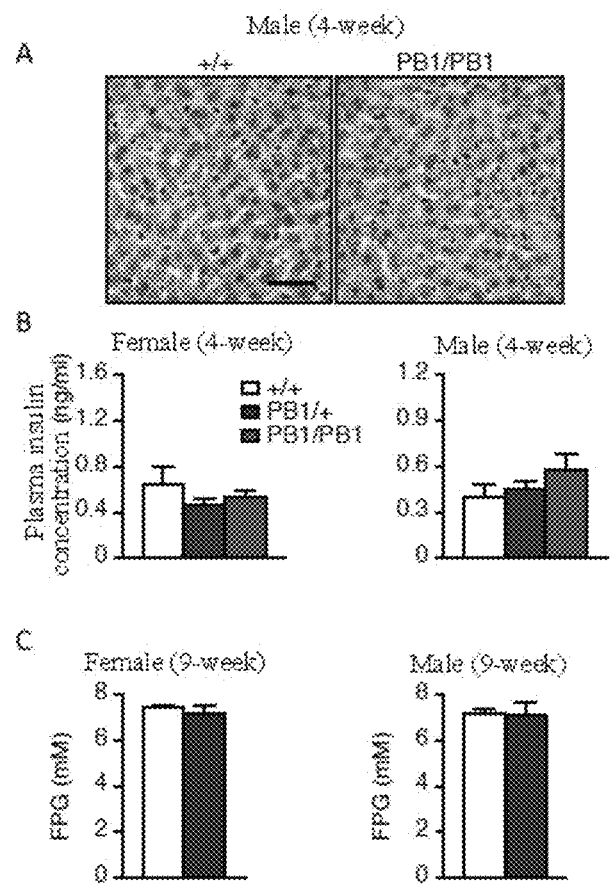
FIG. 11: obesity of GPR45$^{PB1/PB1}$ mice occurs earlier than hepatic steatosiss and diabetes, wherein (A) shows red oil O staining of liver tissue slices of 4-week-old mice, wherein 4-week-old mutant has no hepatic steatosis phenotype and a scale therein is 0.05 mm; (B) shows that concentration of plasma insulin of 4-week-old GPR45$^{PB1/PB1}$ mice is normal; (C) shows that fasting blood-glucose of 9-week-old GPR45$^{PB1/PB1}$ mice is normal; from left to right, a first column line represents wild type (+/+), a second column line represents heterozygote (PB1/+) and a third column line represents homozygote (PB1/PB1); and a number of mice in each group is greater than or equal to 3 and wild-type littermates are selected and used as a control group.

Different from the phenotype of obesity, we did not find the GPR45 mutant mice presented the phenotypes of hepatic steatosiss and impaired glucose homeostasis at an early stage (as shown in FIG. 11). We found that no excessive fat was accumulated in livers of 4-week-old mutant mice and the fasting insulin was not obviously different from that of the wild type mice. We also detected the fasting blood glucose of the mutant mice but no abnormality had been found up to the ninth week of the mice.

To sum up, we proved that the obesity was the primary phenotype of GPR45 mutant mice, indicating that the fat metabolism disorder of the GPR45 mutant mice caused hepatic steatosiss and impaired glucose homeostasis.

Embodiment 9: Discussion on the Disease Mechanism of Obesity in GPR45 Mutant Mice Obesity can result from a shifted balance toward more food intake and less energy expenditure. Therefore, excessive energy intake or decreased energy expenditure will cause obesity. Energy expenditure is divided into basic metabolism consumption, body movement thermogenesis and adaptive thermogenesis. In order to explore the physiological cause of obesity of GPR45 mutant mice, we analyzed energy intake and energy expenditure levels of mice at the beginning of obesity.

Figure 12:
FIG. 12: GPR45$^{PB1/PB1}$ mice present no energy intake abnormality, wherein (A) shows results of ANCOVA analysis on daily food intake of 21-day-old to 33-day-old mice, wherein comparatively food intake is normal when body weight of female mutant mice and wild type mice is 12.58 g, and comparatively food intake is also normal when body weight of male mutant mice and wild type mice is 15.85 g; and (B) shows that a combustion value of feces of 21-day-old mice is normal, in each group, from left to right, a first column line represents wild type (+/+), a second column line represents homozygote (PB1/PB1), a number of mice in each group is greater than or equal to 3 and wild-type littermates are selected and used as a control group.
Figure 13:
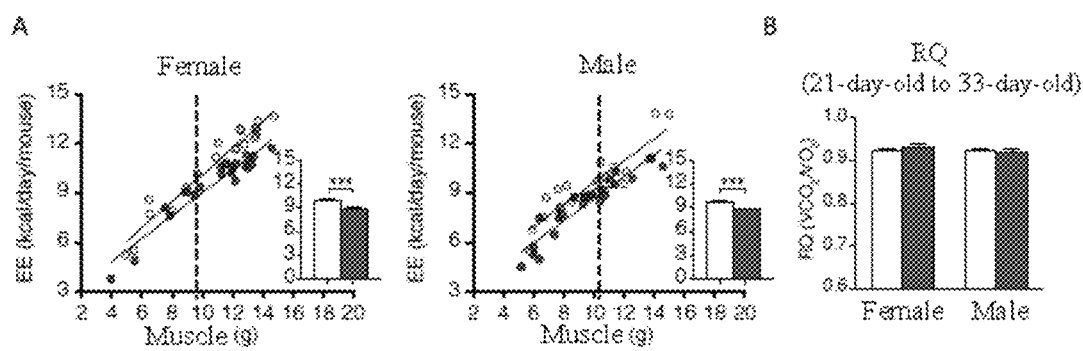
FIG. 13: energy expenditure of GPR45$^{PB1/PB1}$ mice is reduced, wherein (A) shows results of ANCOVA analysis on daily total energy expenditure (EE) of 21-day-old to 33-day-old mice, wherein comparatively total energy expenditure of mutants obviously decreases when muscle weight of female mutant mice and wild type mice is 9.76 g or when body weight of male mutant mice and wild type mice is 10.155 g; (B) shows that a respiratory quotient (RQ) of 21-day-old to 33-day-old mice is normal, in each group, from left to right, a first column line represents wild type (+/+), a second column line represents homozygote (PB1/PB1), a number of mice in each group is greater than or equal to 10, wild-type littermates are selected and used as a control group and $***p<0.001$.

Firstly, we detected food intake of the mutant mice. We detected the daily food intake of mutant mice at ages from 21 days to 33 days and analyzed the food intake of two genotypes at this period by using ANCOVA (analysis of covariance). Results indicated that, under the condition of the same weight, the food intake of the two genotypes was not obviously different (as shown in FIG. 12). Besides, we also analyzed the combustion value of feces of mice, and did not find obvious difference between two genotypes. As proved by the above-mentioned experiments, the energy intake of GPR45 mutant mice was not influenced. No abnormality of the energy intake of obese GPR45 mutant mice indicated us that the energy expenditure of the mutant mice was abnormal. Therefore, we detected 24-hour total energy expenditure (EE) of mutant mice at ages from 21 days to 33 days by using a metabolism cage system (as shown in FIG. 13). As proved by analysis of covariance, under the condition of the same muscle weight, the energy expenditure of the mutant mice was obviously lower than that of the wild type mice and was reflected as that the energy expenditure of female mutant mice and male mutant mice was respectively 10.7% and 9.93% lower than that of the wild type mice. RQ (Respiratory Quotient) is an important index for detecting metabolism fuel utilization, RQs of different metabolism fuels such as sugar, fat and protein are different, and efficiencies of heat production by selecting different fuels to participate in energy metabolism are different. In order to detect whether the metabolism fuels of the mutant mice were different or not, we analyzed the RQs of the mice of the two genotypes at this age period. Results indicated that the RQs of the mice of the two genotypes were not obviously different (as shown in FIG. 13). As proved by the results, the GPR45 mutant mice had no preference to the utilization of metabolism fuels at the beginning of obesity.

Figure 14:
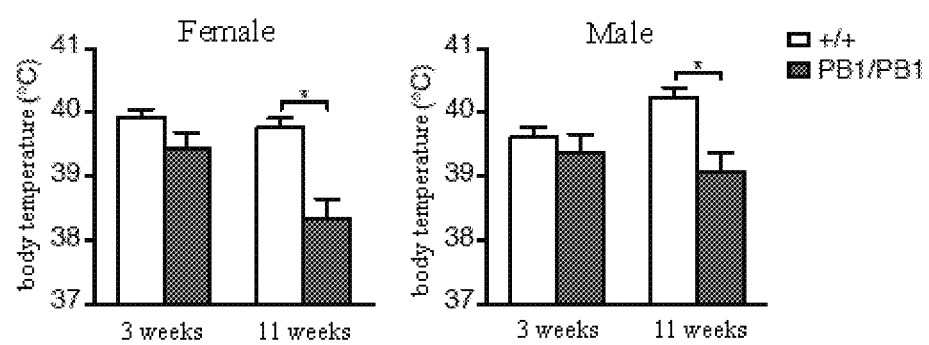
FIG. 14: body temperature decreases after obesity of GPR45$^{PB1/PB1}$ mice occurs, wherein rectal temperature of 3-week-old and 11-week-old mice and body temperature of 3-week-old mutant mice are normal, and body temperature of 11-week-old mutant mice obviously decreases; and in each group, from left to right, a first column line represents wild type (+/+), a second column line represents homozygote (PB1/PB1), a number of mice in each group is greater than or equal to 3, wild-type littermates are selected and used as a control group and $*p<0.05$.

Indexes such as energy expenditure or body temperature of mice in a resting state can reflect basic body energy metabolism level to a certain extent. Considering that the rhythm of the mice under an FVB background is not obvious in normal light-dark cycles, we detected the rectal temperature of mice to reflect the basic metabolism level. Results indicated that the rectal temperature of 3-week-old mutant mice was not obviously different from that of the wild type mice, but the rectal temperature of 11-week-old mutant mice was obviously lower than that of the wild type mice and it was reflected as that the rectal temperature of female and male mutant mice was respectively 1.4° C. and 1.1° C. lower than that of the wild type mice (as shown in FIG. 14). The above-mentioned results indicated that the basis energy expenditure of the obese mutant mice was lower than that of the wild type mice.

Figure 15:
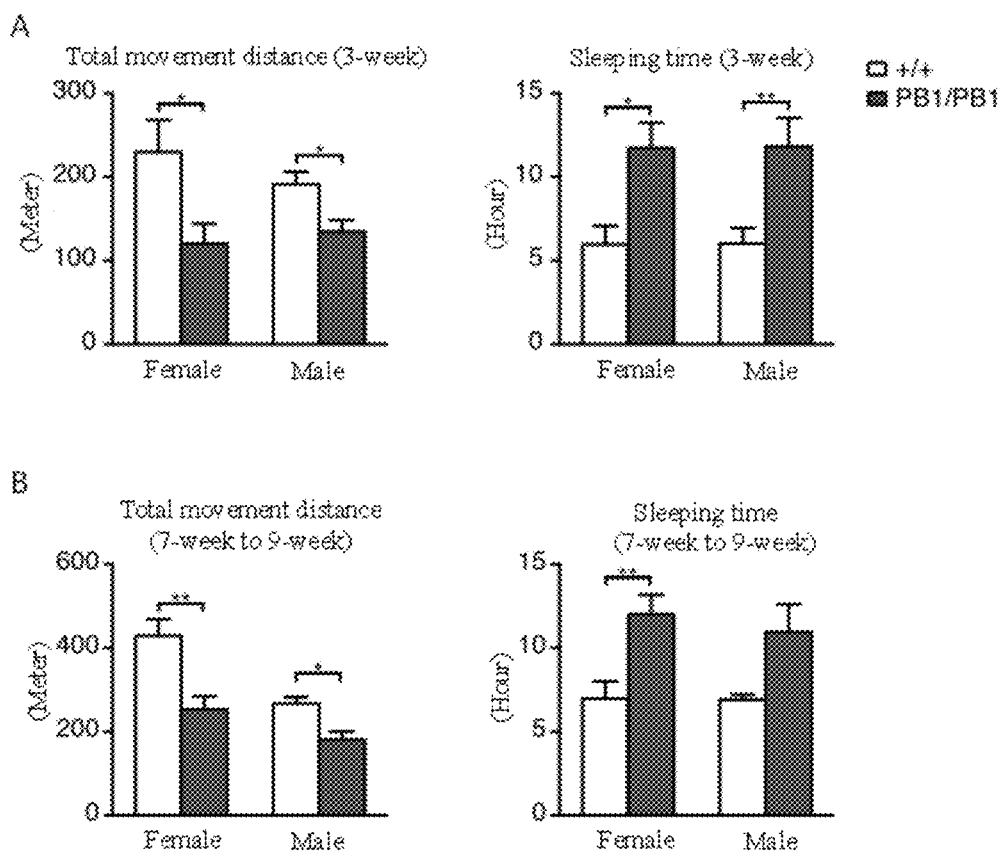
FIG. 15: moving ability of GPR45$^{PB1/PB1}$ mice decreases, wherein (A) shows total movement distance and sleeping time of 3-week-old mice and (B) shows total movement distance and sleeping time of 7-week-old to 9-week-old mice, wherein total moving distance of 3-week-old mice and 7-week-old to 9-week-old mice is obviously shortened, sleeping time obviously increases, in each group, from left to right, a first column line represents wild type (+/+), a second column line represents homozygote (PB1/PB1), a number of mice in each group is greater than or equal to 3, wild-type littermates are selected and used as a control group and $*p<0.05$; $p<0.01$; and $*p<0.001$.

Body movement thermogenesis of experiment mice approximately occupies 40% of total body energy expenditure. In order to carry out a research on whether the movement capacity of GPR45 mutant mice decreased or not, we detected total movement distance and sleeping time of 3-week-old mice within 24 h by using a home-cage system (as shown in FIG. 15). Results indicated that the total movement distance of female mutant mice and male mutant mice within one day was respectively 47.6% and 29.7% shorter than that of the wild type mice; and the sleeping time was two times of that of the wild type mice. 7-week-old or 9-week-old mutant mice also had the similar phenotypes of shortened total movement distance and prolonged sleeping time. The above-mentioned data indicated that the decrease of movement capacity of obese GPR45 mutant mice caused the decrease of energy expenditure to a certain extent.

Figure 16:
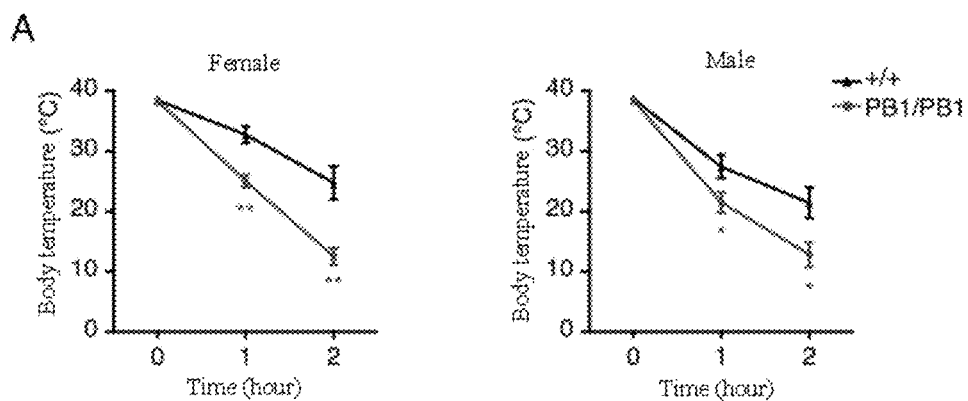
FIG. 16: adaptive thermogenesis of GPR45$^{PB1/PB1}$ mice decreases, wherein according to body temperature decrease curves of 2-week-old mice when being exposed at 4° C. low temperature for 2 h, body temperature of mutant mice when being exposed at 4° C. low temperature quickly decreases; from top to bottom, a top curve represents wild type (+/+), a bottom curve represents homozygote (PB1/PB1), a number of mice in each group is greater than or equal to 5, wild-type littermates are selected and used as a control group and $*p<0.05$; $p<0.01$; and $*p<0.001$.

Adaptive thermogenesis can guarantee that the body temperature of mice is kept to be relatively stable in cold environments. In order to detect whether the adaptive thermogenesis capacity of the mutant mice was abnormal or not, we detected the adaptive cold-induced thermogenesis capacity of 14-day-old mice, we placed the mice in a 4° C. cold environment for 2 h under the condition that food was not provided but drinking water was provided, and change of rectal temperature of the mice was detected. After 2 h, the rectal temperature of the female mutant mice and the male mutant mice respectively decreased by 13.7° C. and 17.3° C., and the body temperature of homozygote mutant mice obviously decreased and respectively decreased by 25.8° C. and 25.6° C. (as shown in FIG. 16). As proved by the experiments, the GPR45 homozygote mutant mice could not maintain the body temperature to be relatively stable under the cold environment, indicating that the decrease of the adaptive thermogenesis capacity of the mutant mice caused the decrease of energy expenditure to a certain extent. To sum up, the energy intake of the GPR45 mutant mice was normal, but the basis metabolism energy expenditure, movement thermogenesis and adaptive thermogenesis capacity decreased, indicating that the blocking of the expression of GPR45 caused the decrease of energy expenditure of the mice instead of the increase of energy intake and thus resulted the occurrence of obesity of the mutant mice.

Figure 17:
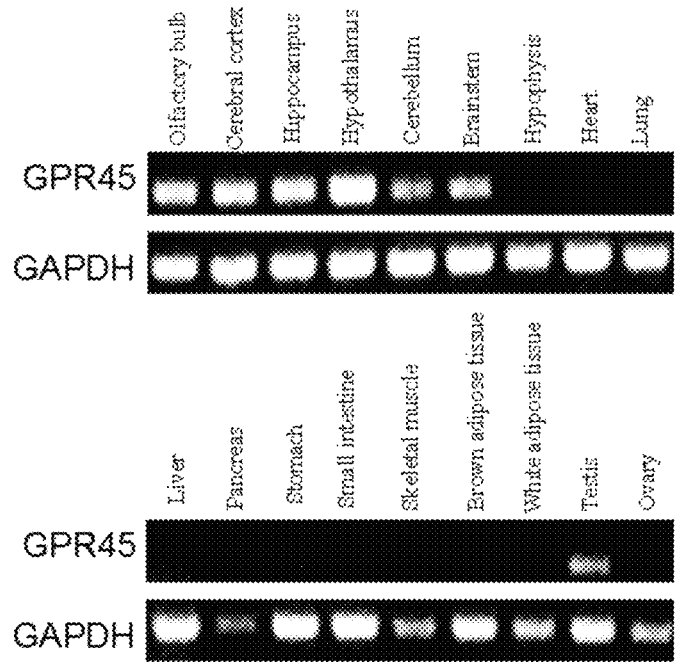
FIG. 17: GPR45 is expressed in a central nervous system and RT-PCR results in each organ of 1-month-old mice are shown; and GPR45 is expressed in a nervous system and testis, and expression of GPR45 is not detected in other peripheral organs.

Embodiment 10: Research on Function of GPR45 During Energy Homeostasis Regulation of Hypothalamus The above-mentioned results indicated that GPR45 played an important role in energy metabolism balance of mice. So, how did GPR45 regulate energy metabolism? We carried out researches on aspects such as expression profile of GPR45, regulation of metabolism-related factors of GPR45 and signal channels in which GPR45 may participate. Firstly we detected the expression profile of GPR45. Past researches indicated that GPR45 had specific expression in brains of mice. We performed reverse transcription PCR by using tissues and organs of 1-month-old mice (the specific method was the same as embodiment 1) and found that GPR45 not only was expressed in each brain area, but also was expressed in testis (as shown in FIG. 17). In the brains of the mice, GPR45 was mainly expressed in olfactory bulbs, cerebral cortexes, hippocampus, hypothalamuses, cerebellums and brainstems. The results indicated that GPR45 played an important role in central nervous systems.

Figure 18:
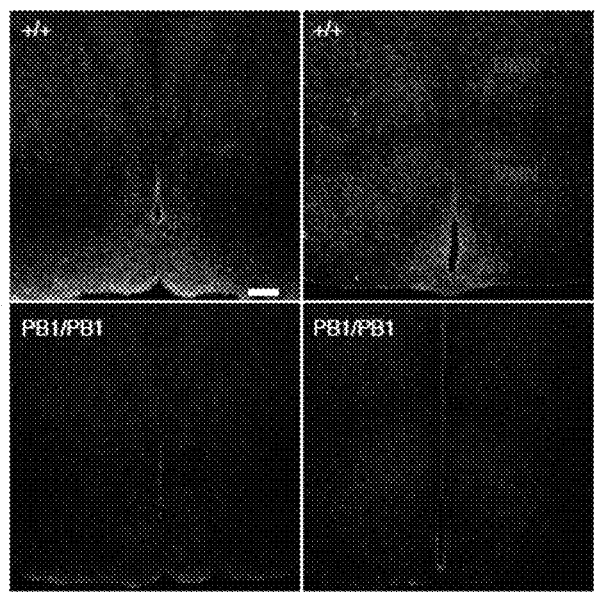
FIG. 18: GPR45 is expressed in an area of hypothalamus, wherein GPR45 antibody immunofluorescence staining is adopted to detect expression of GPR45 in the area of hypothalamus of 14-day-old mice, GPR45 is mainly expressed in suprachiasmatic nuclei (SCN), dorsomedial hypothalamic nuclei (DMN), ventromedial hypothalamic nuclei (VMN) and arcuate nuclei (ARC) of wild type mice (+/+), obvious GPR45 signal expression is not detected in homozygote mice (PB1/PB1) and a scale therein is 0.2 mm.

In view of that hypothalamuses are centers for regulating energy metabolism in nervous systems, we performed immunofluorescence staining to hypothalamus areas of mice by using laboratory self-made antibodies aiming at GPR45 (as shown in FIG. 18). Results indicated that GPR45 was highly expressed in suprachiasmatic nuclei (SCN), dorsomedial hypothalamic nuclei (DMN), ventromedial hypothalamic nuclei (VMN) and arcuate nuclei (ARC). Expression of GPR45 in homozygotes was disrupted. The above-mentioned results indicated that GPR45 participated in the regulation of energy metabolism by the hypothalamus.

Figure 26:
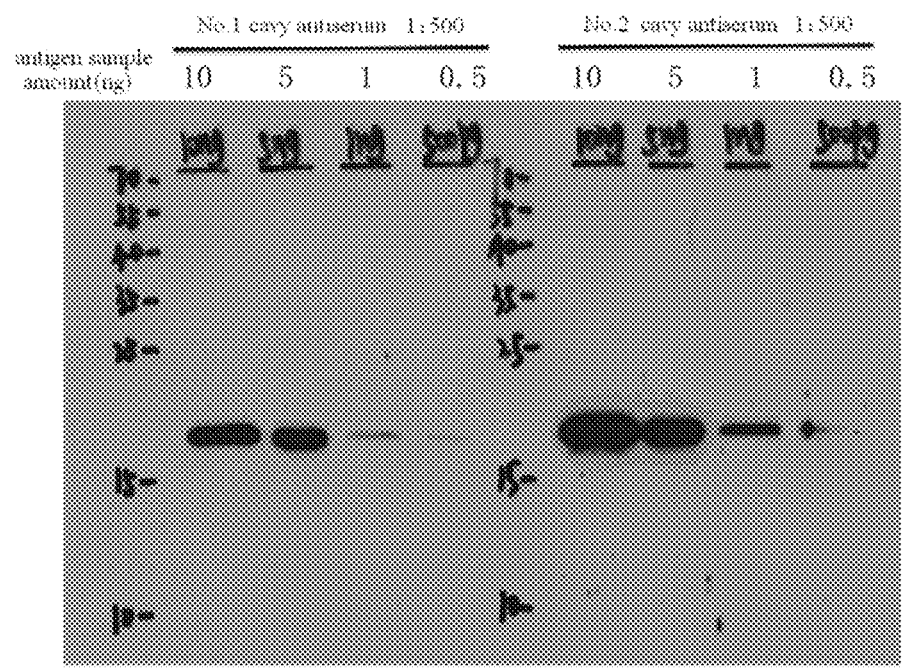
FIG. 26: antigens can still be detected by antiserums after the antigens are diluted to 0.5 ng, immune signals of No. 2 cavy are stronger and it fully indicates that the prepared polyclonal antibody has extremely high sensitivity.

A method for preparing the laboratory self-made antibodies aiming at GPR45 specifically comprised the following steps:

(1) directly preparing a separated antigen peptide as shown by an amino acid sequence SEQ ID NO:33 through a method of chemically synthesizing polypeptide, MACNSTPMGT YEHLLLNVSN TLDPGDTPLS APLRISGYTE FPAERN-TVRK NAVRVHNQSD SLDLRQLTGA GLRRLRRQQQ QASLDLSFKT KSAFSRRFYY SASFYTPHTF QILPKV-PERI QRKIQPSTIY VCNENQSAVL E (SEQ ID NO:33);

(2) performing immunization to cavies by using the prepared antigen peptide as an immunizing antigen:

taking two cavies as an example:

1st day: injecting CFA (Complete Freund's Adjuvant) containing 500 ug of antigen;

14th day: injecting IFA (Incomplete Freund's Adjuvant) containing 250 ug of antigen;

28th day: injecting IFA (Incomplete Freund's Adjuvant) containing 250 ug of antigen;

42th day: injecting IFA (Incomplete Freund's Adjuvant) containing 250 ug of antigen;

56th day: injecting IFA (Incomplete Freund's Adjuvant) containing 250 ug of antigen;

70th day: executing the cavies by bloodletting, preparing serum, providing 100 ul of antiserum, diluting antigen according to a gradient shown in FIG. 26, and performing Western Blot detection (antiserum concentration 1:500). Results indicated that the antigen could still be detected by the antiserum when the antigen was diluted to 0.5 ng and immune signals of No. 2 cavy were stronger. It fully indicated that the prepared polyclonal antibody had extremely high sensitivity.

Figure 27:
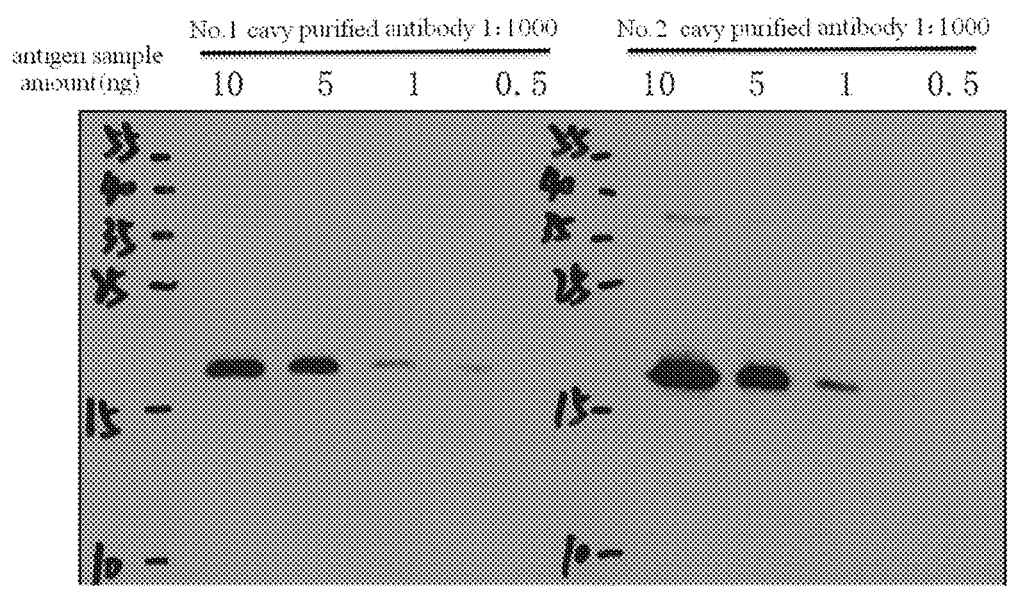
FIG. 27: antigens can still be detected by antiserums after the antigens are diluted to 0.5 ng, immune signals of No. 2 cavy are stronger and it fully indicates that the prepared polyclonal antibody has extremely high sensitivity.

11th week: purifying the antibody: purifying the antiserum by using a Protein A/G affinity column, dissolving the purified antibody in PBS (pH 7.3) containing 0.02% of sodium azide and 50% of glycerin; providing 1 ml of purified antibody of No. 1 cavy (7.83 mg/ml) and 1 ml of purified antibody of No. 2 cavy (8.09 mg/ml); and diluting the antibody according to a gradient shown in FIG. 27 and performing Western Blot detection (purified antibody concentration 1:1000). Results indicated that the antigen could still be detected by the antiserum when the antigen was diluted to 0.5 ng and immune signals of No. 2 cavy were stronger. It fully indicated that the prepared polyclonal antibody had extremely high sensitivity.

Embodiment 11: GPR45 Mutation Influences Expression of POMC Neuropeptide in Hypothalamus and POMC Neuron Activity Neuropeptides such as AgRP, NPY, POMC, CART, CRH, TRH, BDNF, MCH and Orexin regulating energy metabolism were expressed in hypothalamus areas. In order to detect whether the above-mentioned neuropeptides participated in the regulation of energy metabolism by GPR45, we detected expression amounts of the above-mentioned neuropeptides by using hypothalamuses of 14-day-old mice. Specific sequences of primers used by RT-PCR (the specific method was similar to embodiment 1) during amplification were as follows:

| GPR45 | GPRP1 | ATGGCCTGTAACAGCACAC | SEQ ID NO. 9 |
| | GPRP2 | ACAGTGATGAGGGTGATGG | SEQ ID NO. 10 |
| AgRP | AgRP-F | GCGGAGGTGCTAGATCCA | SEQ ID NO. 11 |
| | AgRP-B | AGGACTCGTGCAGCCTTA | SEQ ID NO. 12 |
| NPY | NPY-F | CTCCGCTCTGCGACACTAC | SEQ ID NO. 13 |
| | NPY-B | AATCAGTGTCTCAGGGCT | SEQ ID NO. 14 |
| POMC | POMC-F2 | CTGCTTCAGACCTCCATAGATG | SEQ ID NO. 15 |
| | POMC-B2 | ATCTCCGTTGCCAGGAAAC | SEQ ID NO. 16 |
| CRAT | CRAT-F1 | AAACGCATTCCGATCTACG | SEQ ID NO. 17 |
| | CRAT-B1 | GGAAAGAGGGAATATGGGAACC | SEQ ID NO. 18 |
| CRH | CRH-F2 | CTCTCTGGATCTCACCTTCC | SEQ ID NO. 19 |
| | CRH-B2 | CTTGTGTGCTAAATGCAGAATC | SEQ ID NO. 20 |
| TRH | TRH-F1 | TCTTGAGGAAAGACCTCCAGCG | SEQ ID NO. 21 |
| | TRH-B1 | AGGCTCCCACTTCTCCCAAATC | SEQ ID NO. 22 |
| BDNF | BDNF-F1 | CATGAAAGAAGTAAACGTCCAC | SEQ ID NO. 23 |
| | BDNF-B1 | TCGATGACGTGCTCAAAAG | SEQ ID NO. 24 |
| MCH | pMCH-F1 | GGGGAAAGCCTTTCAGAAG | SEQ ID NO. 25 |
| | pMCH-B1 | CTGTGTGGACTCAGCATTC | SEQ ID NO. 26 |
| Orexin | Orexin-F2 | CTTTCCTTCTACAAAGGTTCCC | SEQ ID NO. 27 |
| | Orexin-B2 | GCTTTCCCAGAGTCAGGATAC | SEQ ID NO. 28 |
| GAPDH | GAPDH-L1 | TGTTCCTACCCCCAATGTGTCC | SEQ ID NO. 7 |
| | GAPDH-R1 | GGAGTTGCTGAAGAAGTCGCAG | SEQ ID NO. 8 |

Figure 19:
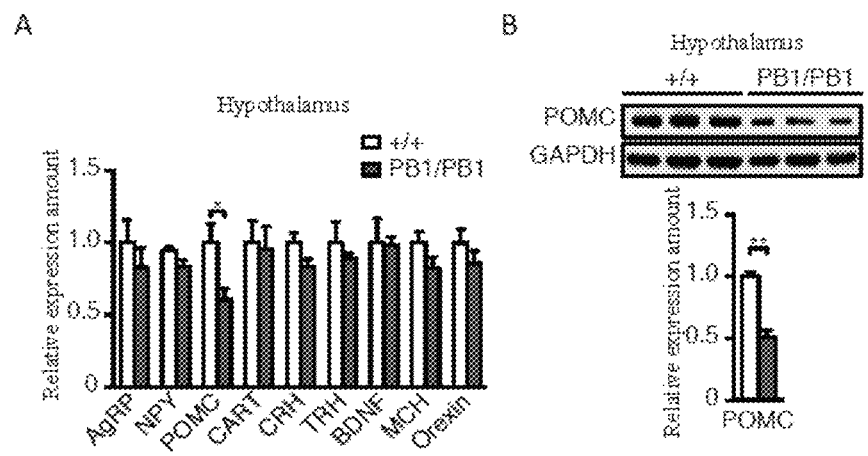
FIG. 19: GPR45 mutation causes POMC expression to decrease, wherein (A) shows expression amounts of hypothalamic neuropeptide of 14-week-old mice, RT-PCR results indicate that POMC expression amounts in hypothalamus of homozygote mice decrease; (B) shows expression amounts of POMC protein in hypothalamus of 14-week-old mice, wherein WB results indicate that expression amounts of POMC protein in hypothalamus of homozygote mice decrease; in each group, a first column line represents wild type (+/+), a second column line represents homozygote (PB1/PB1), a number of mice in each group is greater than or equal to 3, wild-type littermates are selected and used as a control group, GAPDH is used as an internal reference and $*p<0.05$; and $**p<0.01$.

Results indicated that, in the hypothalamuses of mutant mice, except that the expression amount of POMC decreased by 40%, the expression amounts of other neuropeptides were not obviously changed. We further detected the expression level of POMC protein in the hypothalamuses of 14-day-old mutant mice. As shown by results of Western Blot experiments, the expression amount of the POMC protein in the hypothalamuses of the mutant mice decreased about 50%. The above-mentioned results indicated that GPR45 could promote the expression of POMC (as shown in FIG. 19).

Figure 22:
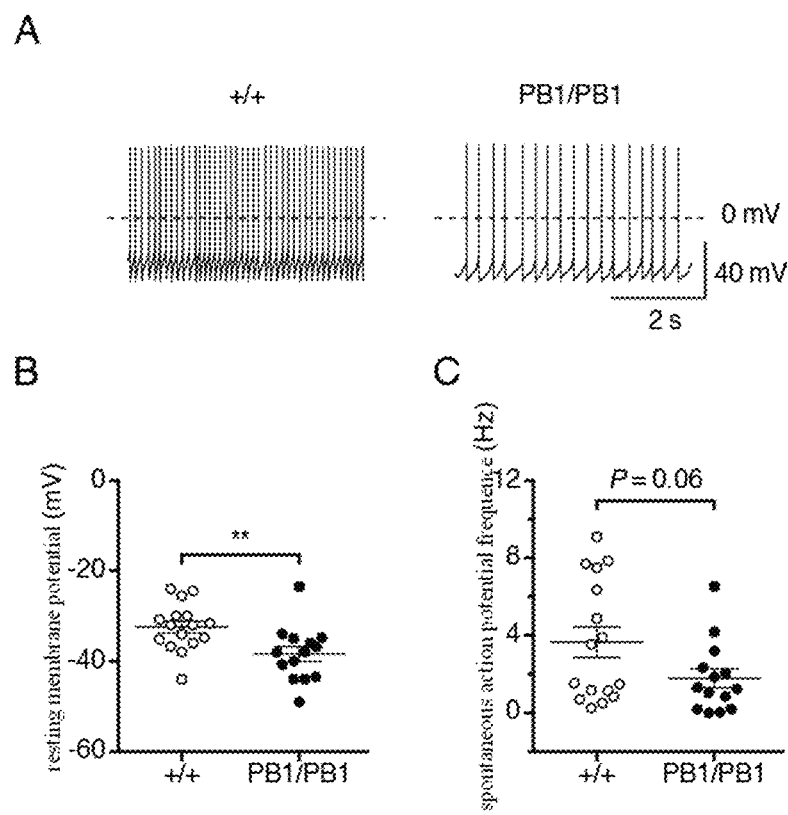
FIG. 22: GPR45 mutation inhibit the activity of POMC neurons; (A) the decrease of resting membrane potential of hypothalamas POMC neurons of 14-week-old $GPR45^{PB1}$ mice is detected in the patch clamp tests; (C) the decrease of action potential of hypothalamas POMC neurons of 14-week-old $GPR45^{PB1}$ mice; the first column represents wild type (+/+), the second column represents homozygote (PB1/PB1), each group of neurons is greater than or equal to 14, the number of mice in each group is greater than or equal to 3.

The decrease of α-MSH, the shear product of hypothalamas POMC, is always along with the electrophysiological of POMC neuron. The electrophysiological of POMC neuron of hypothalamas of 14-day-old mice is detected by patch clamp experiment, the result of voltage clamp shows that resting membrane potential of neurons in homozygous hypothalamas decrease obviously, the frequency of spontaneous action potential decrease (as shown in FIG. 22). The above mentioned results show that GPR45 could regulate the activity of POMC neurons.

Embodiment 12: GPR45 Cells Autonomously Regulate Expression of POMC

Figure 20:
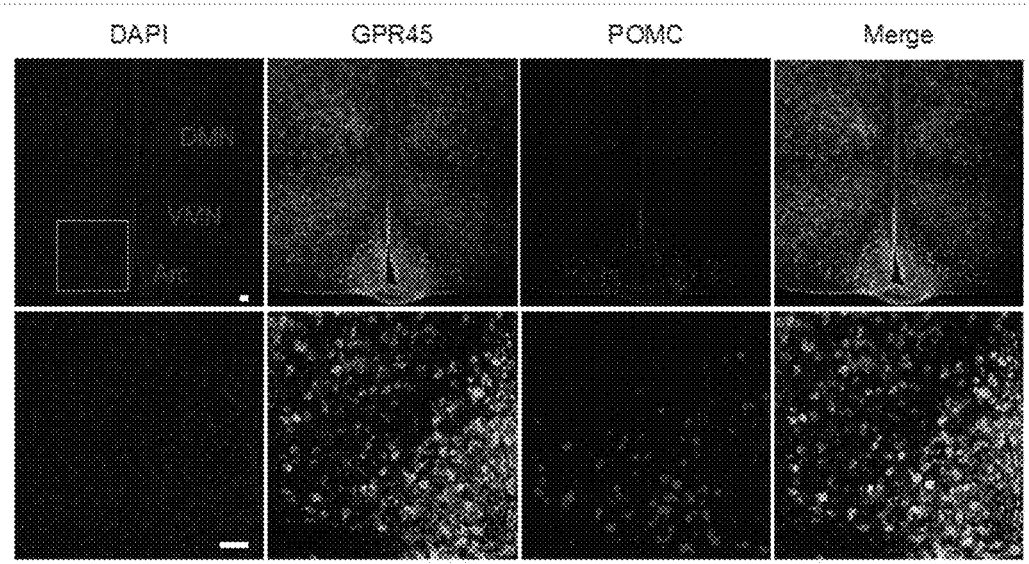
FIG. 20: GPR45 is expressed in POMC neurons, wherein according to POMC and GPR45 antibody immunofluorescence staining of brain slices of 14-week-old wild type mice, GPR45 (green) is expressed in DMN, VMN and ARC, and POMC (red) is expressed in ARC; and in ARC, about 80% of POMC neurons express GPR45; and frames in a bottom line are regionally enlarged views of top frames, cell nuclei are stained by DAPI (blue) and a scale therein is 0.05 mm.

In hypothalamus, POMC was specifically expressed in an ARC area. As shown by results of our immunofluorescence, GPR45 was also expressed in ARC and thus GPR45 might regulate the expression of POMC in POMC neurons. In order to prove this assumption, we detected the expression of GPR45 in the POMC neurons of the arcuate nuclei areas of the hypothalamuses by using 14-day-old wild type mice (as shown in FIG. 20). As shown by results of POMC and GPR45 antibody immunofluorescence co-staining, in arcuate nuclei of the wild type mice, about 80% of POMC positive neurons expressed GPR45. The results indicated that GPR45 cells autonomously regulate the expression of POMC.

In order to further prove the autonomous regulation of POMC by GPR45, we detected the expression of POMC in primary culture cells of the hypothalamuses of the mice.

A method for separating and culturing the primary culture cells of the hypothalamuses of the mice comprised the following steps:

executing pregnant mice which were pregnant for 16.5-18.5 days by breaking necks, quickly taking out embryo, cutting off heads to strip off brains, putting the brains in ice-cooled 1×HBSS (Invitrogen Company) buffer solution and placing the buffer solution on ice; after all brains were stripped off, carefully stripping off meninx under a stereoscope by using pointed pliers, removing cerebrums, cerebellums, brainstems and ganglia, taking out hypothalamuses, putting the hypothalamuses in ice-cooled 1×HBSS (Invitrogen Company) buffer solution and placing the buffer solution on ice;

after all hypothalamuses were collected, cutting the hypothalamuses into pieces by using Vannas ophthalmological scissors, and digesting at 37° C. for 20-30 min by using 5 ml of 0.125% pancreatic enzyme;

transferring a cell mass to 5 ml of planting culture medium: DMEM (Gibco Company)+10% FBS (Hyclone Company)+2 mM L-glutamine (Gibco Company)+50 U/ml P+S (Gibco Company), gently blowing and beating the cell mass for 20 times by using a dropper and standing the cells for 10 min;

gently blowing and beating the settled cell mass again for 10-20 times by using 5 ml of fresh planting culture medium until the cell mass was blown scattered, and standing the cells for 10 min;

collecting cell suspension obtained after blowing and beating at two times, filtering the cell suspension by using a 70 um cell strainer (Corning Company) and collecting the cells in a 50 ml tube;

blowing the cells scattered, then counting the cells and spreading the cells in a 12-well plate, wherein each well had $5*10^5$ cells; and before the cells were spread into the 12-well plate, treating the 12-well plate at room temperature for 4 h by using 0.05 mg/ml D polylysine (Sigma Company), and washing the 12-well plate for three times by using sterilized double distilled water;

changing solution after cell grown for 4 h and using NB culture medium: Neurobasal Medium (Gibco Company)+ 2% B27 (Gibco Company)+2 mM L-glutamine (Gibco Company)+50 U/ml P+S (Gibco Company), wherein each well had 1 ml;

changing half of solution for one time every three days by using NB culture medium, i.e., changing 0.5 ml at every time; and performing subsequent processing after the cells grown for 7 days.

Figure 21:
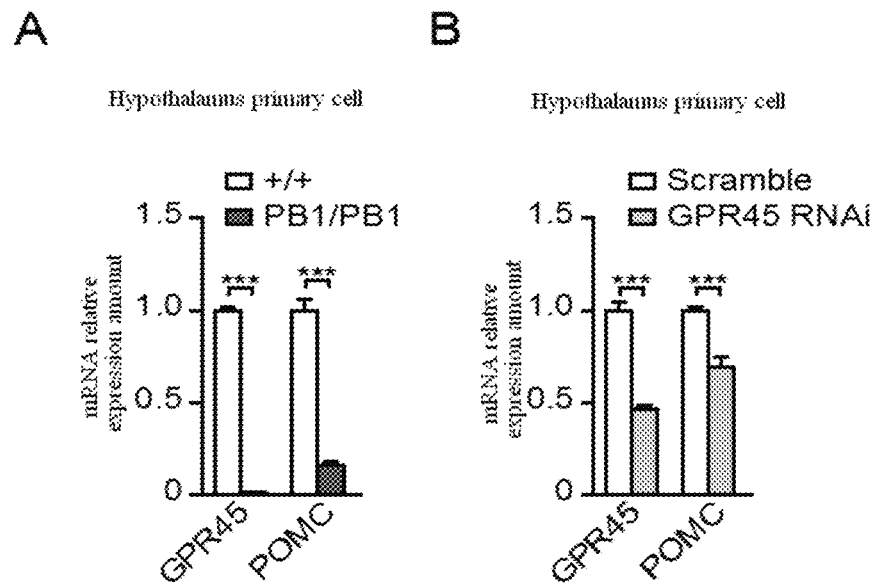
FIG. 21: suppression of expression of GPR45 causes POMC expression to decrease, wherein (A) shows expression amounts of POMC in primary cultured cells of hypothalamus of fetal mice, wherein RT-PCR results indicate that expression amounts of POMC in primary cultured cells of hypothalamus of homozygote fetal mice decrease; from left to right, a first column line represents wild type (+/+), a second column line represents homozygote (PB1/PB1), a number of samples in each group is greater than or equal to 3, primary cultured cells of hypothalamus of brood wild type fetal mice are selected and used as a control group, GAPDH is used as an internal reference and *$p<0.001$; (B) shows knockdown of expression of GPR45 in primary cultured cells of hypothalamus of wild type fetal mice by using an RNA interference technology, wherein RT-PCR results indicate that expression amounts of POMC decrease by knocking down the expression of the GPR45 in the primary cultured cells of the hypothalamus of the wild type fetal mice, and scramble groups are as shown by white column lines; GPR45 RNA interference experiment groups (GPR45 RNAi) are as shown by grey column lines, a number of samples in each group is greater than or equal to 5, GAPDH is used as an internal reference and *$p<0.001$.

For detection of POMC expression, primary cell RNA was extracted to perform reverse transcription to obtain cDNA, then real-time quantitative PCR detection was performed, and experiment steps were the same as embodiment 11. As shown by results in FIG. 21, in the primary culture cells of the hypothalamuses of mutant fetal mice, the expression amount of POMC decreased by 84%.

Expression of GPR45 in the primary culture cells of the hypothalamuses of the wild type fetal mice was blocked by using an RNA interference technology, and a specific method comprised the following steps:

after the primary cells of hypothalamuses of the mice grown for 7 days, respectively diluting Lipofectamine RNAiMAX (Invitrogen Company) and siRNA (GenePharma Company) by using OPTI-MEM culture medium (Gibco Company) with the same volume, then uniformly mixing according to a ratio of 1:1, and standing for 5 min at room temperature until an siRNA-liposome complex was formed; dropping the OPTI-MEM culture medium containing the siRNA-liposome complex into cell culture medium, performing transfection for 72 h and then collecting the cells. During an experiment at each time, at least three times of well repetition were performed to each kind of siRNA. The cells in each well of the 12-well plate were finally added into 100 ul of OPTI-MEM culture medium containing 10 pmol siRNA+3 ul Lipofectamine RNAiMAX compound objects.

suppress the expression of POMC, indicating that GPR45 cells could autonomously regulate the expression of POMC.

Figure 23:
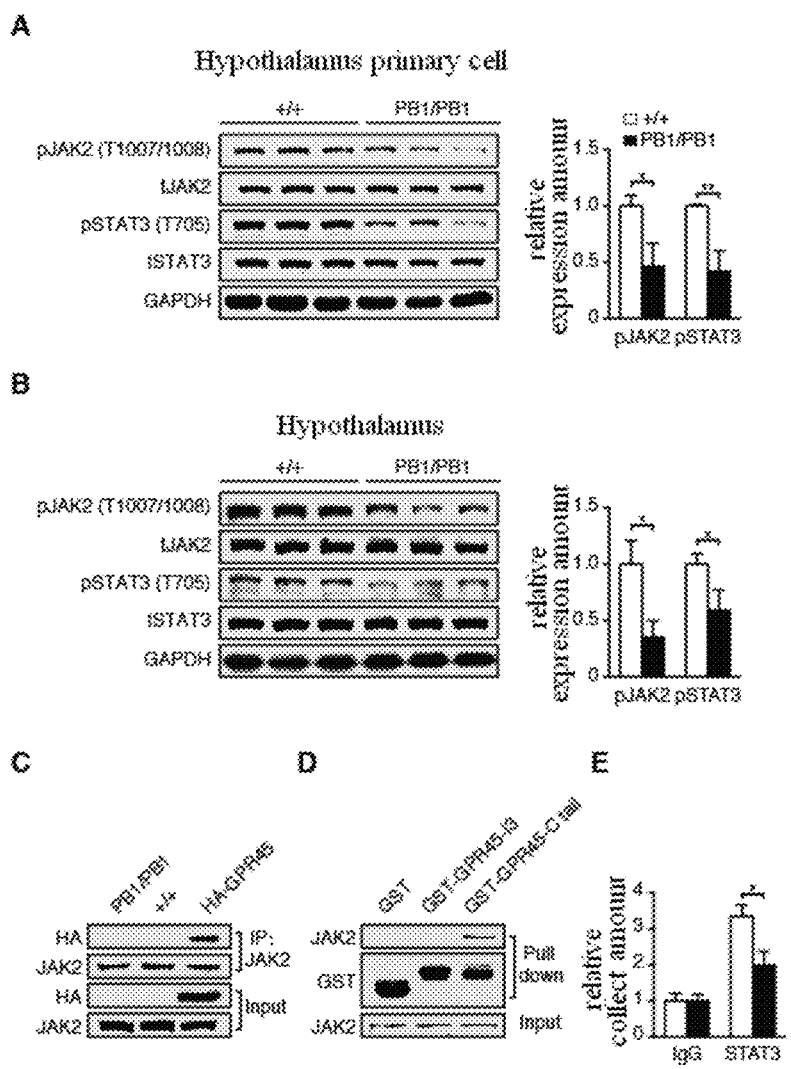
FIG. 23: GPR45 regulates the expression of POMC through JAK/STAT in hypothalamas, (A) WB detected that the phosphorylation level of JAK2 and STAT3 decreases in the primary culture cell of homozygous fetal rate's hypothalamas; (B) WB detected that the phosphorylation level of JAK2 and STAT3 of 14-day-old homozygote hypothalamas decreases, the right graph is the statistical graph of the expression level, in each group, from left to right, the first column represents wild type (+/+), the second column represents homozygote (PB1/PB1), a wild-type littermates is used as a control, the number of mice in each group is greater than or equal to 3, total protein expression level of JAK2 and STAT3 is used as standard internal reference, *$p<0.05$; **$p<0.01$; (C) Endogenous JAK2 protein is used as a bait to perform immune coprecipitation by JAK2 antibody in the sample of the brain protein of adult NSE::GPR45 transgenic mice. HA antibody is used to detect GPR45. The protein sample of mice brain of the homozygote (PB1/PB1) and wild type (+/+) do not express HA-GPR45 fusion protein is used as a negative control; (D) binding experiment in vitro shows GPR45 and JAK2 are bind directly. Prokaryotic expressed and purified His-taged JAK2 could bind to the C tail of GPR45, but could not bind the third cyclic (i3) of GPR45. GST antibody is used to test GST-taged GPR45 fragment; (E) In the chromatin immunoprecipitation tests performed by STAT3 antibody, it is found that comparing with the same age wild type mice, the quantity of the promoter area of POMC gene collected by transcription factor STAT3 in 14-day-old homozygous hypothalamas decrease obviously. Rabbit IgG is used as negative control, from left to right, the first column represents wild type (+/+), the second column represents homozygote (PB1/PB1), *$p<0.05$.

We further investigate the mechanism of the regulation of the expression of POMC by GPR45. As mentioned above, the enhancer and promoter area in the upstream of POMC gene possess two STAT3 response elements. The transcription of POMC in hypothalamas could responses the regulation of JAK/STAT pathway. Specific knockout of STAT3 in nervous system could lead to the decrease of expression level of POMC, the decrease of consuming of energy and obesity. Simultaneously, JAK2 could bind to various kind of GPCR directly, regulate the downstream signal pathway. Therefore, we detect the phosphorylation level of JAK2 in the primary culture cell of homozygous fetal rate's hypothalamas. It is found that comparing with the wild type mice, the phosphorylation level of JAK2 decrease by 53.2%, and phosphorylation level of STAT3 decrease by 57.9% (as shown in FIG. 23). The phosphorylation level test of JAK2 and STAT3 in the hypothalamas of 14-day-old GPR45$^{PB1/PB1}$ mice shows that the phosphorylation level decrease by 64.6% and 40.9% respectively (as shown in FIG. 23). We further test whether GPR45 could bind with JAK2 (as shown in FIG. 23). Binding experiment in vitro is further performed, it is found that JAK2 could bind the C tail of GPR45, but could not bind the third cyclic (i3) of GPR45 (as shown in FIG. 23). Furthermore, the chromatin immunoprecipitation tests shows that the quantity of the promoter area of POMC gene collected by transcription factor STAT3 in GPR45 homozygous hypothalamas decrease obviously (as shown in FIG. 23). The above mentioned results indicate that JAK/STAT signal pathway involved in the transcription regulation of POMC through GPR45.

In order to further prove that POMC signals acted on the downstream of GPR45 to suppress the occurrence of obesity, we monitored changes of body weight and body fat of GPR45 mutant mice by injecting MTII in third Intraventriculars of the GPR45 mutant mice. MTII is an agonist of MC3R/MC4R, can simulate a function of a POMC shorn product α-MSH and plays a role of suppressing appetite and promoting energy metabolism. We found that, by daily injecting MTII in third Intraventriculars of adult GPR$^{PB1/PB1}$ obese mice, the increase of the body weight of the GPR$^{PB1/PB1}$ mice could be suppressed. After three days after MTII was injected, the body weight of GPR45$^{PB1/PB1}$ mice could be reduced to the level of the body weight of the wild type mice. After six days after MTII was injected, the body weight of the mutant mice injected with MTII was decreased by 13.6% relative to the body weight before injection, and the body weight of the wild type mice injected with MTII was decreased by only 1.8% relative to the body weight before injection. When the mutant mice and wild type mice of control groups were injected with equal

| siRNA | name | RNA Oligo sequence | |
|---|---|---|---|
| GPR45-siRNA | Sense strand | 5'-CCGACAUCAUGCUGUCUUUAUTT-3' | SEQ IDNO. 29 |
| | Antisense strand | 5'-AUAAAGACAGCAUGAUGUCGGTT-3' | SEQ IDNO. 30 |
| Scrambled siRNA | Sense strand | 5'-UUCUCCGAACGUGUCACGUTT-3' | SEQ IDNO. 31 |
| | Antisense strand | 5'-ACGUGACACGUUCGGAGAATT-3' | SEQ IDNO. 32 |

Figure 24:
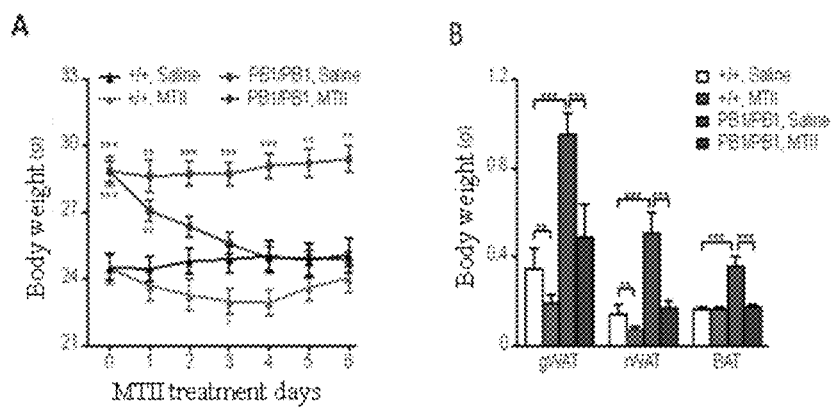
FIG. 24: obesity is suppressed by injecting MTII into third Intraventricular of GPR45 mutant mice, wherein (A) shows that body weight decreases after six days after MTII is injected into third Intraventricular of adult male GPR45 homozygote mice; (B) shows that fat content decreases by injecting MTII into third Intraventricular of adult male GPR45 homozygote mice; in each group, from left to right, a first column line represents a control group of wild type mice (+/+) into which normal saline is injected, a second column line represents an experiment group of wild type mice (+/+) into which MTII is injected, a third column line represents a control group of homozygote mice (PB1/PB1) into which normal saline is injected, a fourth column line represents an experiment group of homozygote mice (PB1/PB1) into which MTII is injected, a number of mice in each group is greater than or equal to 5, wild-type littermates are selected and used as a control group and *$p<0.05$; $p<0.01$; and *$p<0.001$.

As shown by results, the expression amount of POMC decreased by 30.7% when the expression amount of GPR45 decreased by 53.4%. The result indicated that GPR45 could amounts of normal saline, the body weight was not influenced. After six days after administration, compared with the mice injected with normal saline in the control group, the weight of gonadal white adipose tissues, retroperitoneal white adipose tissues and interscapular brown adipose tissues of the mutant mice injected with MTII respectively decreased by 48.5%, 66.7% and 50.4%. The weight of gonadal white adipose tissues and retroperitoneal white adipose tissues of the wild type mice injected with MTII respectively decreased by 44.1% and 50.9%, and the weight of interscapular brown adipose tissues increased by 0.4%. As shown by the above-mentioned results, $GPR45^{PB1/PB1}$ mice were more sensitive to MTII activated POMC signals, indicating that the POMC signals participated in the regulation of energy metabolism by GPR45 (as shown in FIG. 24).

Embodiment 13: Application of Obese Mouse Model of the Present Invention

The obese mouse model established in the embodiment of the present invention can be used for screening weight-reducing drugs.

Firstly, Codonopsis mother liquor was prepared and a method comprised the following steps:
1) taking 5 kg of Codonopsis, adding pure water with weight which was 6 times of weight of medicines and soaking the medicines for 14 h;
2) performing decoction and maintaining a boiling state for 45 min;
3) performing filtration, reserving filtrate, adding pure water with weight which was 4 times of weight of medicines into medicine residues, performing decoction again and maintaining a boiling state for 80 min;
4) performing filtration, abandoning the medicine residues and reserving filtrate; and
5) concentrating filtrate obtained in steps 3 and 4 to 1420 ml (i.e., final concentration of 3.5 g/ml), and preserving concentrated liquor at −80° C.

A method for establishing FSHRPB mutant mice was as follow:

FSHR is follicle-stimulating hormone receptor. For mice with this gene which was knocked out, it was ever reported that poor female gonad development (ANDRE'E DIERICH et al., PNAS, 1998) and obesity (NATALIA DANILOVICH et al., Endocrinology, 2000) occurred. A PB transposon was inserted into a first intron of a gene of FSHRPR mutant mice cultivated by us, and according to detection by using a small animal nuclear magnetic resonance spectrometer, it was found that an obesity symptom such as female body fat content increase also occurred in this strain like the gene knocked-out mice.

The above-mentioned Codonopsis mother liquor was administrated to the FSHRPB mutant mice and obese mice established in the above-mentioned embodiment, the same effect of reducing content of body fat of obese mice could be achieved. A specific method was as follow:

Animals: FSHRPB homozygote mutant female mice/obese mice established in the above-mentioned embodiment of the present invention, the mice were divided in cages at age of 21 days, each cage had 5 mice, and administration was performed at age of 7 week. Codonopsis preparation: mother liquor concentration was 3.5 g/ml*28.5 ml, and mother liquor was dissolved in 300 ml of acidified water (the method for decocting the mother liquor was the same as described above).

Experiment group: one cage of mice (5 mice), 300 ml of prepared solution of codonopsis. Control group: one cage of mice (5 mice), 300 ml of acidified water was administrated.

Duration: 4 weeks.

Figure 25:
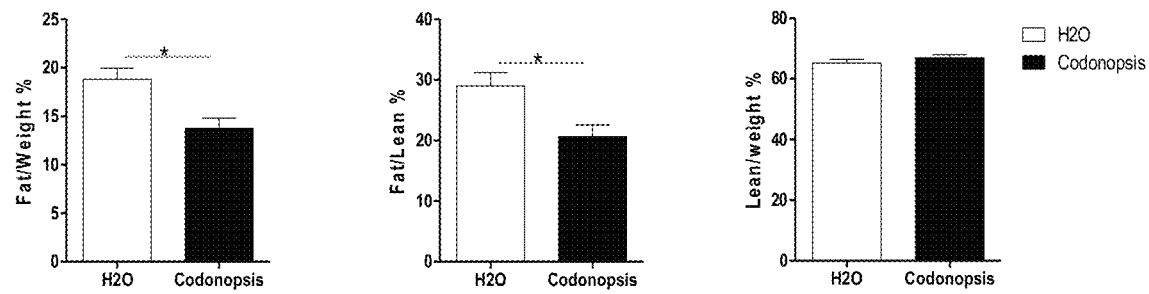
FIG. 25: Codonopsis can reduce body fat of obese mice.

Experiment contents: cage was changed weekly and content of body fat was detected by using a small animal nuclear magnetic resonance spectrometer after the 4th week was ended. As shown by results in FIG. 25, the content of body fat in both two kinds of obese mice decreased and it was consistent with the report that Codonopsis can be used as a weight-reducing drug in the prior art. It indicated that the obese mice established by the present invention could be used for screening weight-reducing drugs.

The above-mentioned embodiments are just preferred embodiments of the present invention. The above-mentioned embodiments are only used for exemplarily describing the principle and effect of the present invention instead of formally and substantively limiting the present invention. It should be pointed out that one skilled in the art can make various improvements and supplements without departing the method of the present invention, and these improvements and supplements shall also be viewed as the protection scope of the present invention. Equivalent variations such as a few of changes, modifications and evolutions made by one skilled in the art according to the technical contents disclosed above without departing the spirit and scope of the present invention shall be considered as equivalent embodiments of the present invention; and in addition, any equivalent variation such as change, modification and evolution made to the above-mentioned embodiments according to the substantive technology of the present invention shall still belong to the scope of the technical solution of the present invention.

What is claimed is:

1. A method for establishing a mouse or rat obesity model, comprising:
   (a) providing a mouse or rat strain with a single copy of a piggyBac (PB) transposon inserted in its genome,
   (b) providing a transgenic mouse or rat strain whose genome comprises a sequence encoding PB transposase,
   (c) mating the mouse strain in (a) with the mouse strain in (b) or mating the rat strain in (a) with the rat strain in (b) to generate offspring mice and rats, respectively,
   (d) identifying PB transposon insertion sites by reverse PCR in offspring mice and rats, and
   (e) selecting an offspring mutant mouse or rat that is homozygous knockout in the GPR45 gene by the PB transposon insertion at the position of 34,038 base pairs upstream of the second exon of the GPR 45 gene or at the position of 54,466 base pairs upstream of the second exon of the GPR45 gene, and thereby establishing a mouse or rat obesity model.

2. A mouse or rat obesity model that is established by the method of claim 1.

3. The mouse or rat obesity model of claim 2, further develops to form a mouse or rat model of hepatic steatosis or a mouse or rat model of diabetes.

4. The method of claim 1, wherein the PB transposon is PB [Act-RFP] transposon.

5. The method of claim 4, wherein the sequence encoding PB transposase is Act-PBase.

* * * * *